United States Patent [19]

John, Jr. et al.

[11] Patent Number: 5,074,151

[45] Date of Patent: Dec. 24, 1991

[54] ULTRASONIC TUBE INSPECTION STATION

[75] Inventors: Clarence D. John, Jr., Penn Hills Township, Allegheny County; Richard S. Wengewicz, Murrysville, both of Pa.

[73] Assignee: Westinghouse Electric Corp., Pittsburgh, Pa.

[21] Appl. No.: 555,347

[22] Filed: Jul. 20, 1990

[51] Int. Cl.[5] .................... G01N 29/24; G01N 29/26; G01N 29/10
[52] U.S. Cl. ........................................ 73/622; 73/628; 73/629; 73/640; 73/866.5
[58] Field of Search ................. 73/622, 627, 628, 620, 73/638, 629, 644, 640, 866.5

[56] References Cited

U.S. PATENT DOCUMENTS

| | | | |
|---|---|---|---|
| 3,678,735 | 7/1972 | Boulanger et al. | 73/644 |
| 4,052,887 | 10/1977 | Sheridan et al. | 73/592 |
| 4,520,672 | 6/1985 | Saint-Amour | 73/622 |
| 4,740,146 | 4/1988 | Angelbeck | 73/622 |

FOREIGN PATENT DOCUMENTS 2338658  7/1973  Fed. Rep. of Germany ........ 73/622

Primary Examiner—John E. Chapman
Assistant Examiner—Rose M. Finley

[57] ABSTRACT

A tube inspection station includes a receptacle having walls defining a cavity for holding energy coupling liquid and receiving an object to be inspected in the liquid. At least one wall of the receptacle has a longitudinal bore defined and extending therein from an opening at the top thereof above the cavity and a transverse bore extending through the wall. The transverse bore intersects with the longitudinal bore and opens at both interior and exterior surfaces of the wall. The station also includes a transducer operable for sending waves of energy from its first end into the cavity toward the object and receiving echos of energy at the first end from the object for measuring a parameter of the object. Also, the transducer is operable for transmitting input and output signals at its second end. Further, the station includes a mounting assembly removably mounted in the longitudinal and transverse bores of the wall and removably mounting the transducer in the transverse bore such that the first end of the transducer communicates with the cavity and the second end of the transducer communicates with the exterior of the receptacle.

5 Claims, 22 Drawing Sheets

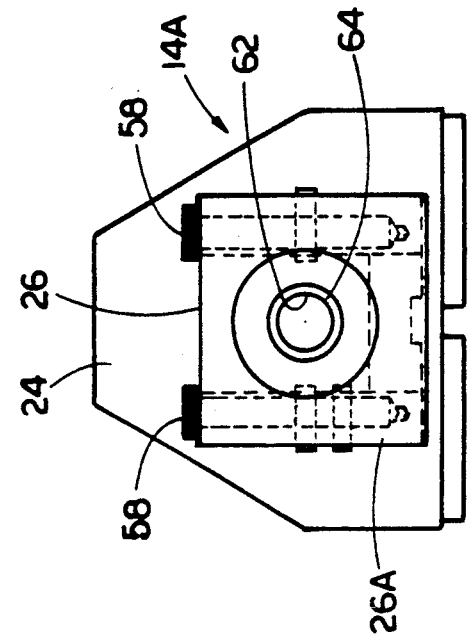
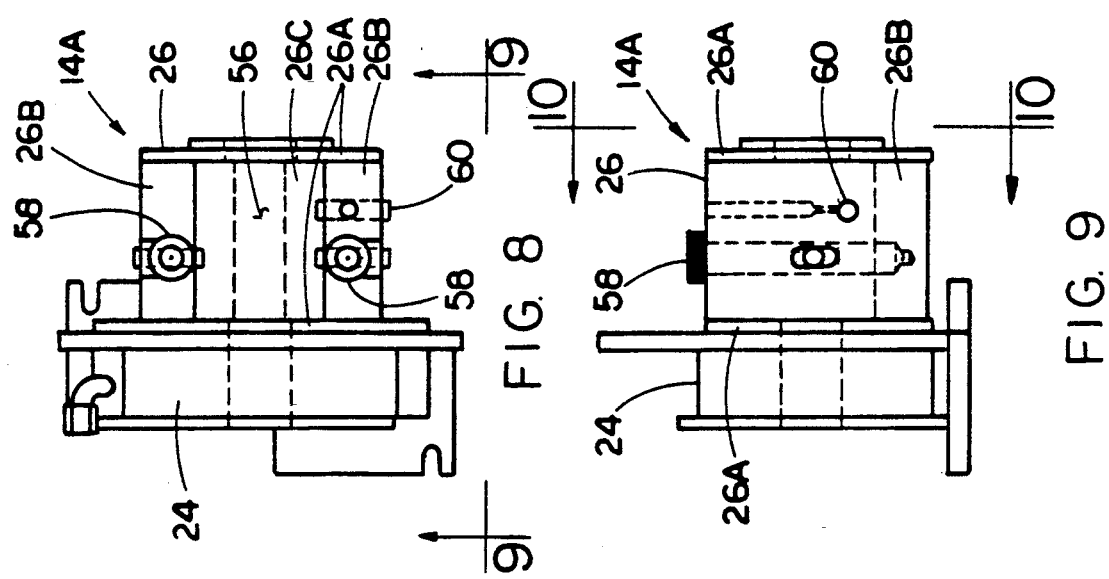

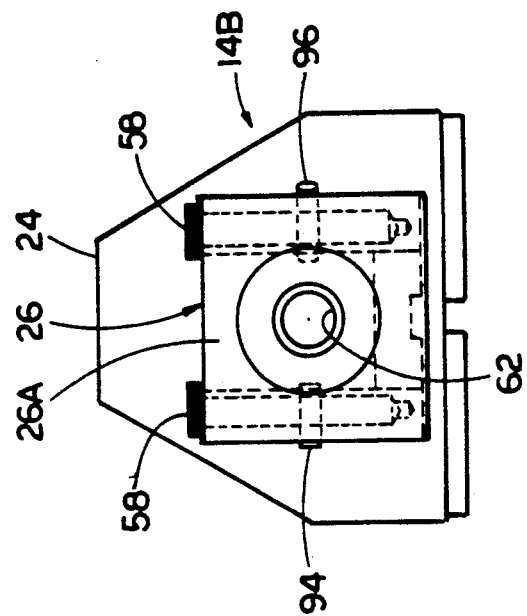
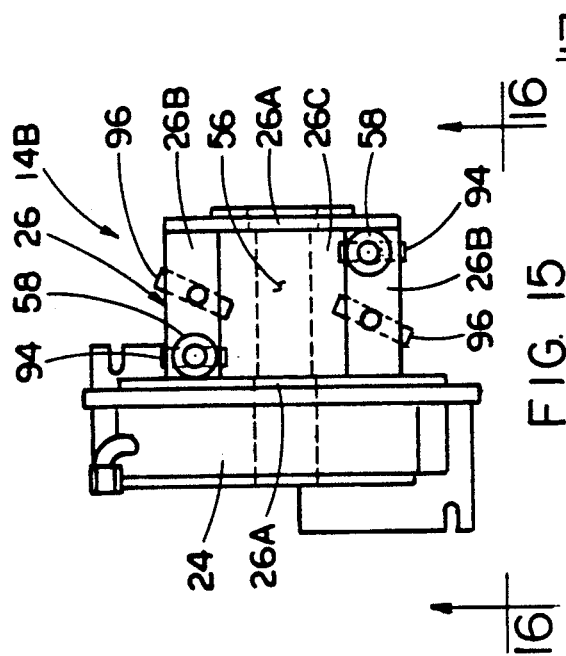
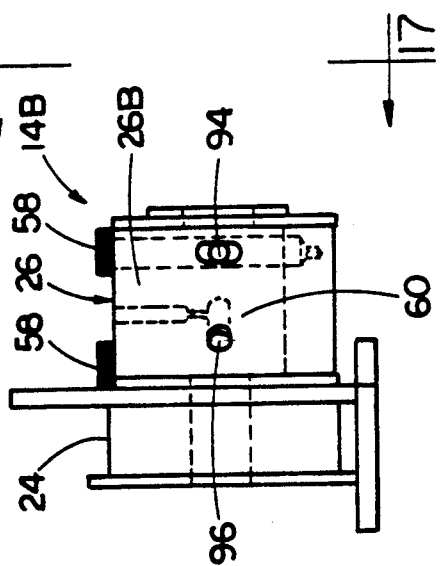

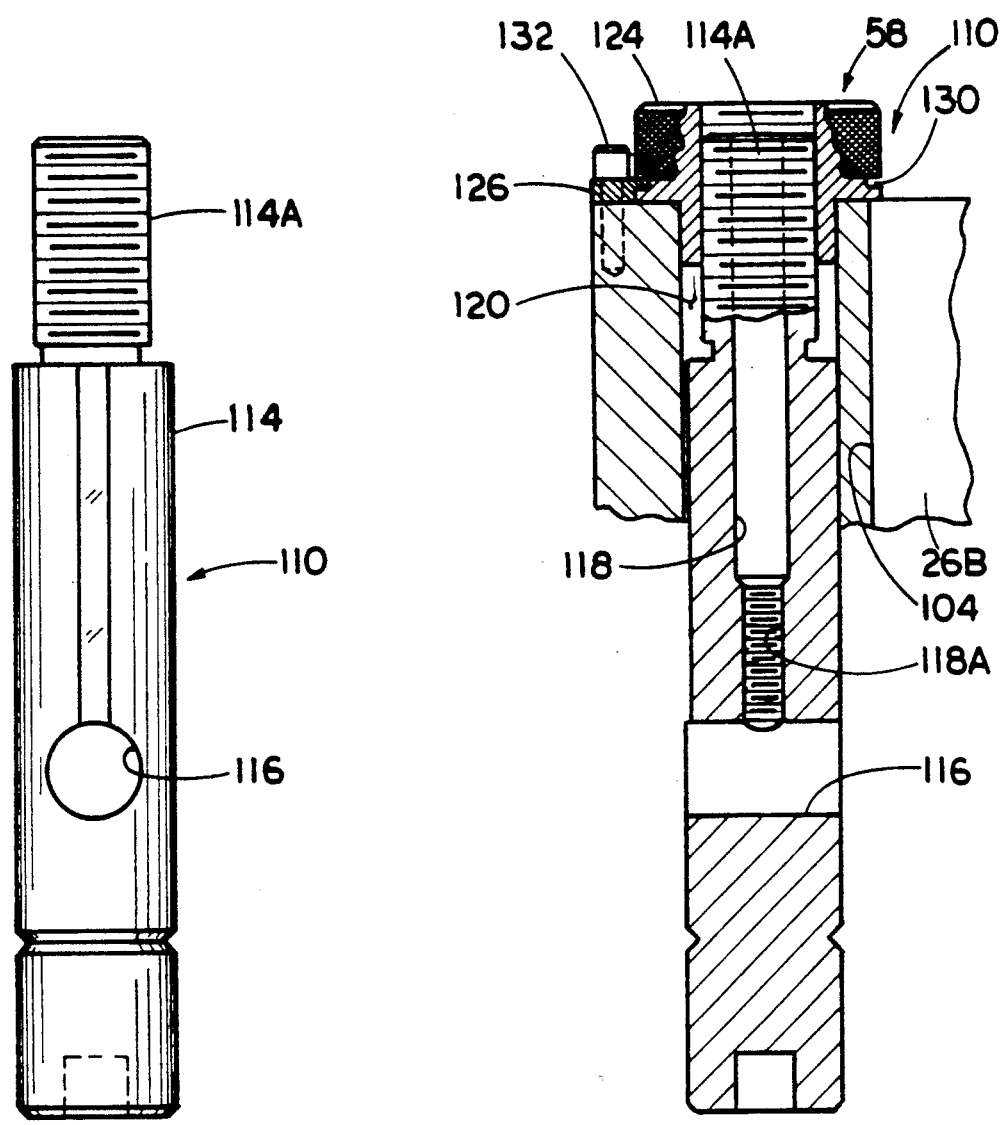
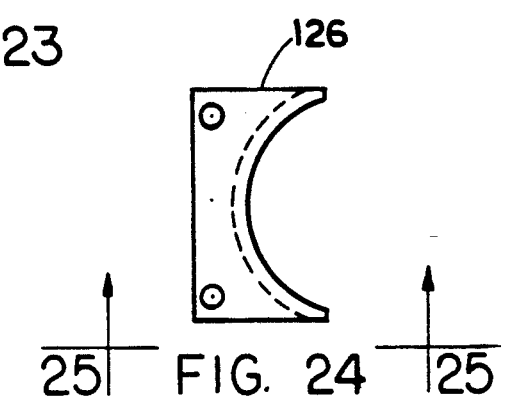
FIG. 23 FIG. 22
FIG. 24
FIG. 25

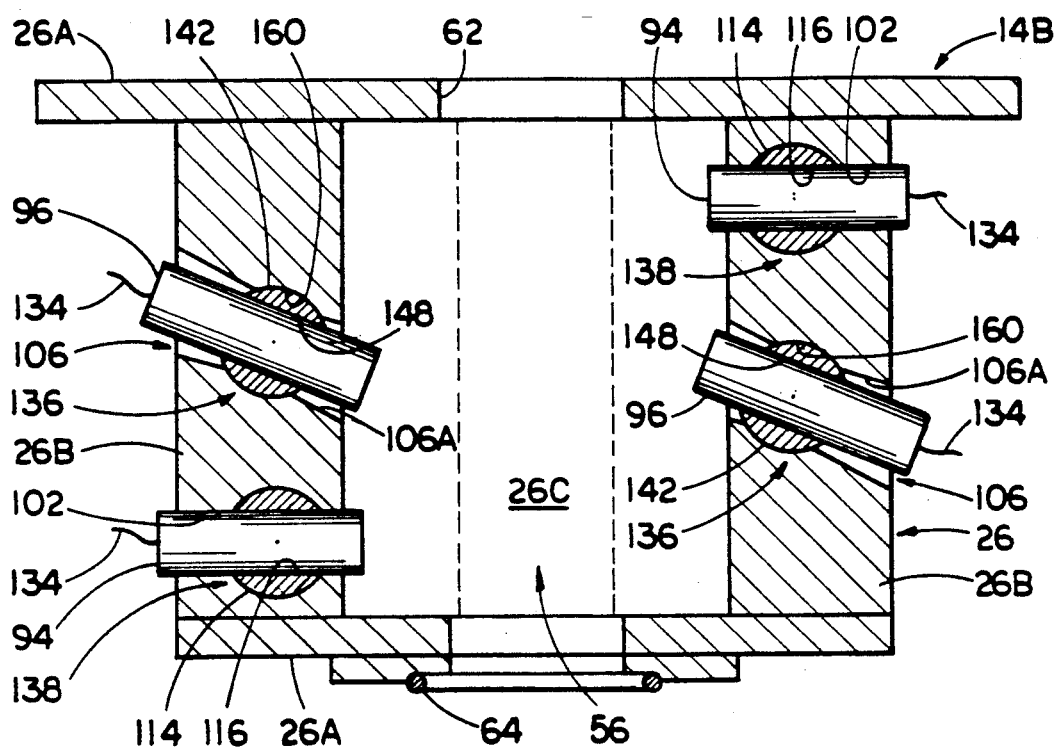
FIG. 40
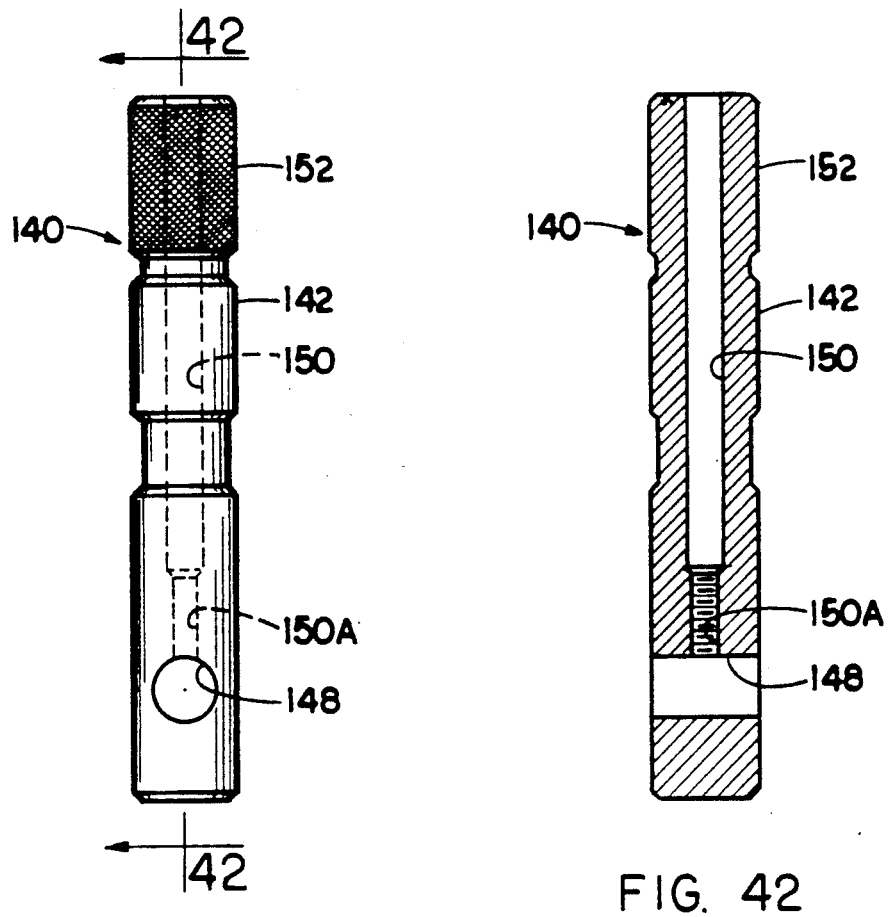
FIG. 41
FIG. 42

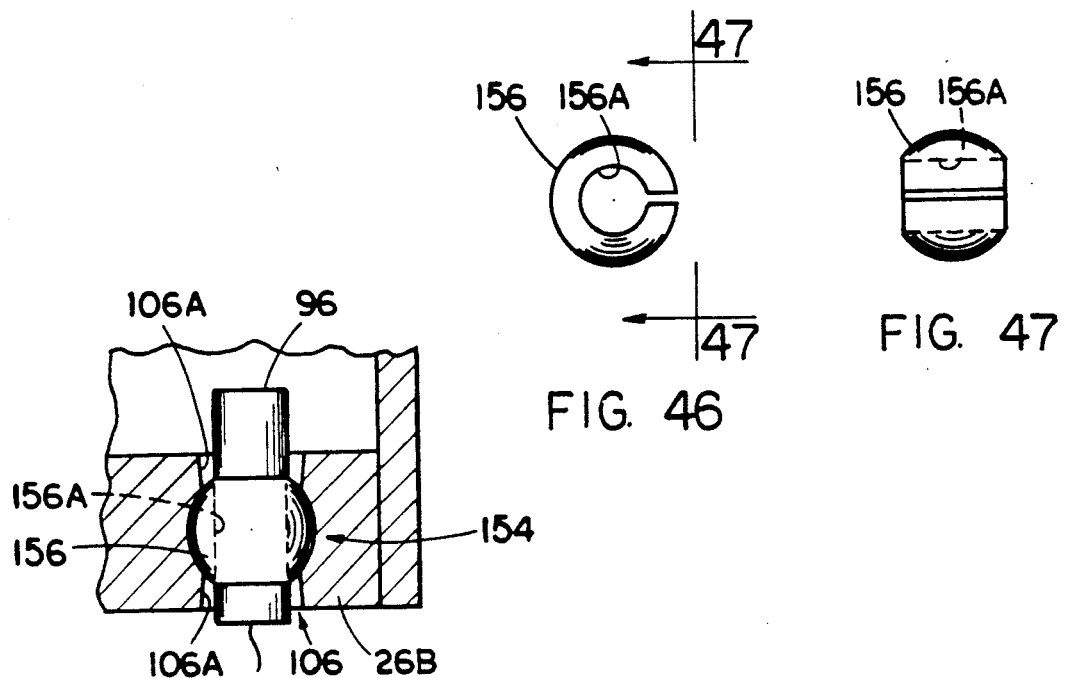
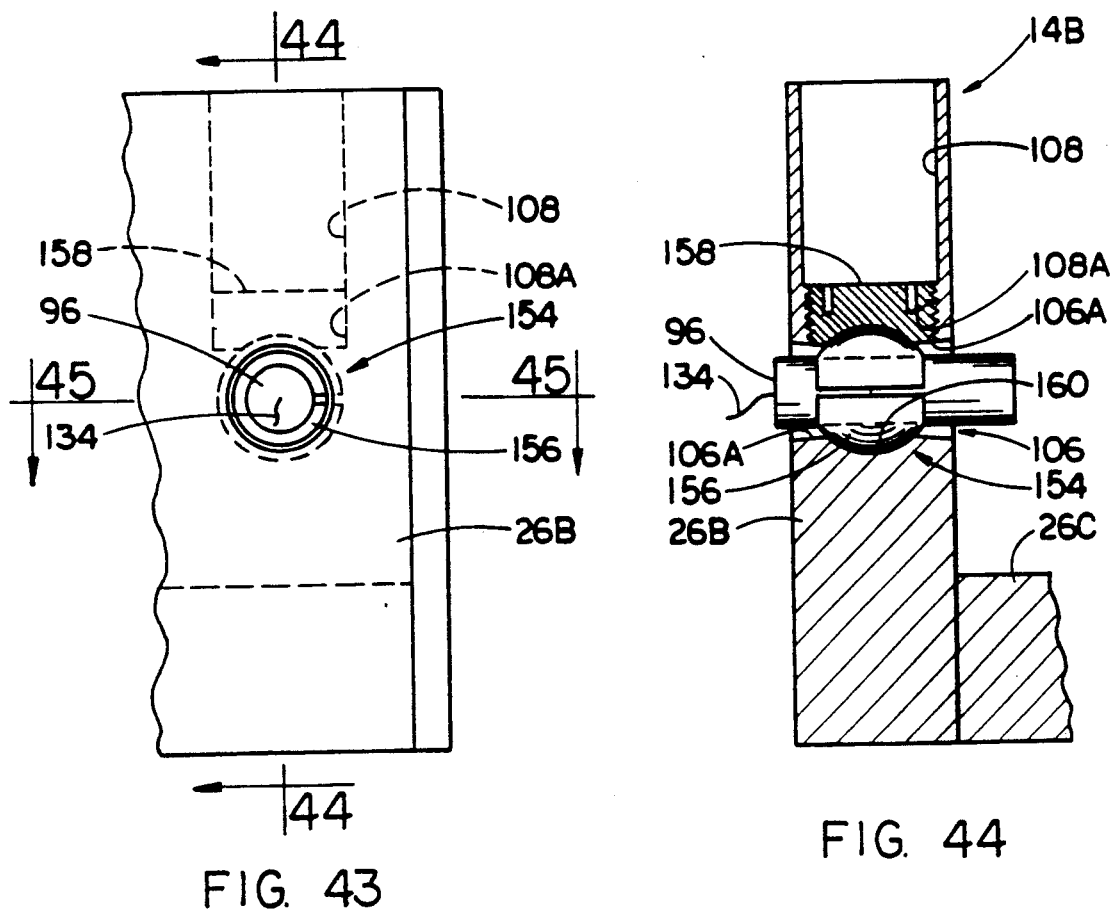

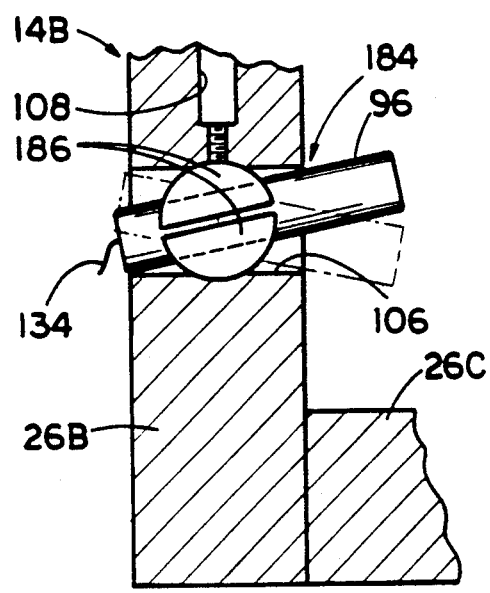
FIG. 58
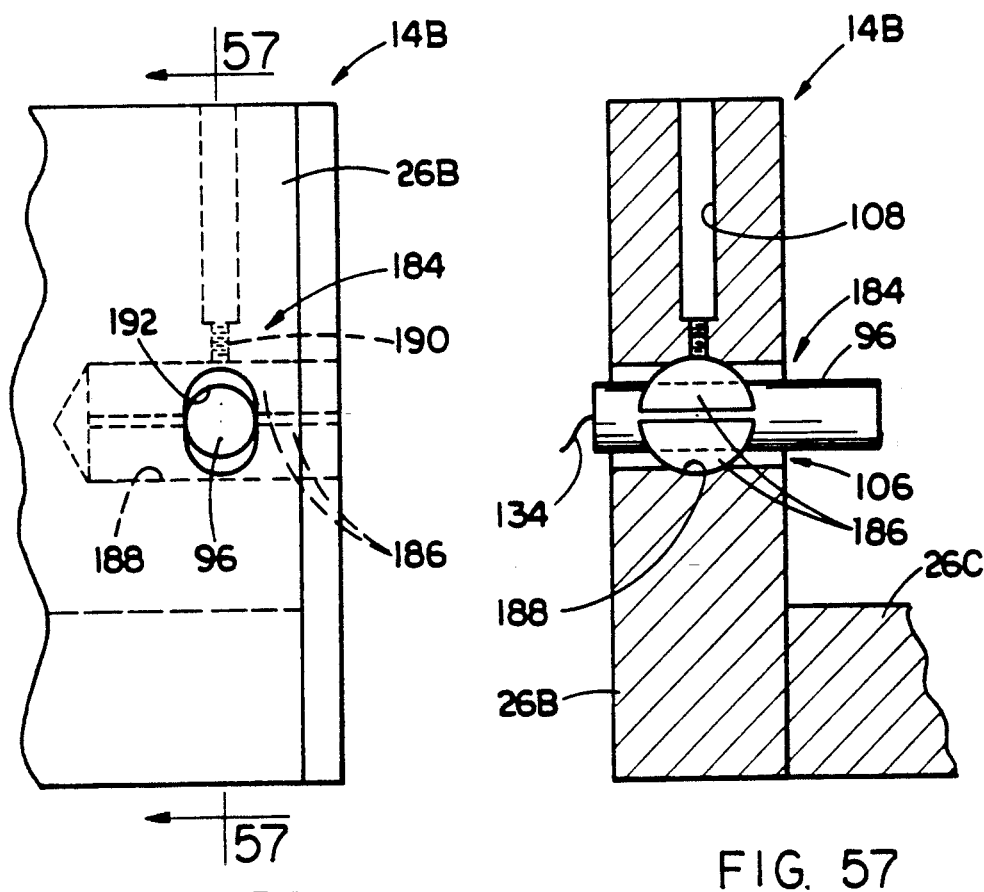
FIG. 56
FIG. 57

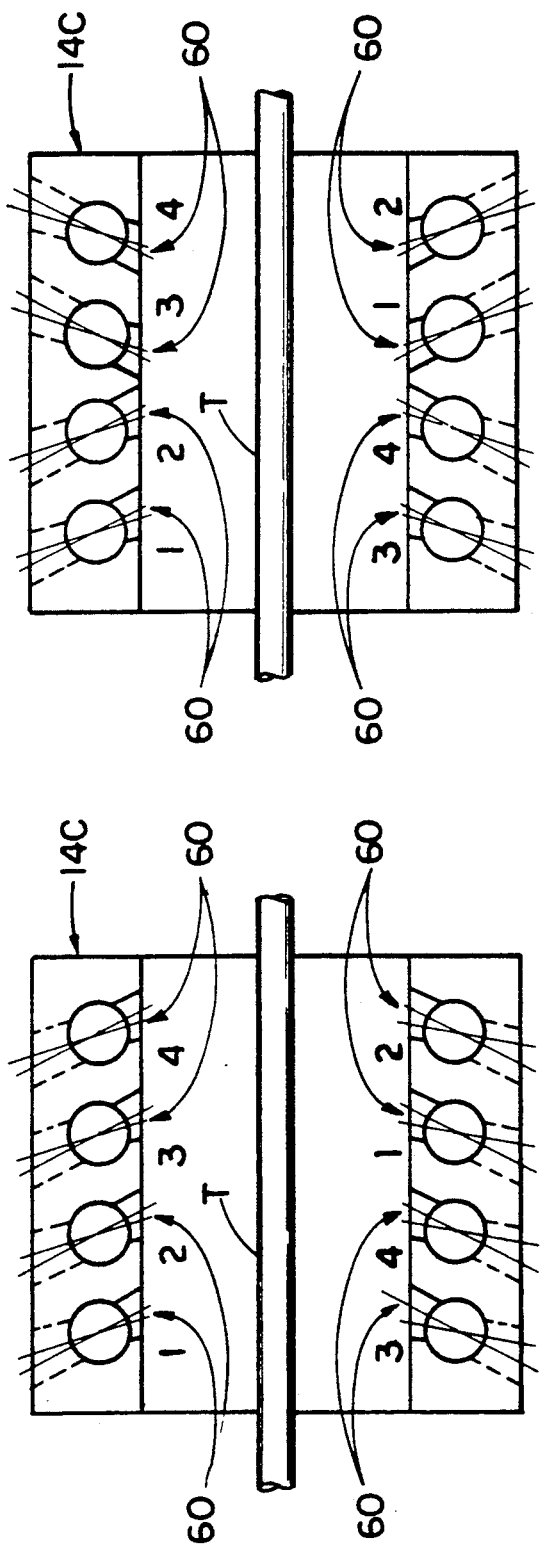
FIG. 64
FIG. 65
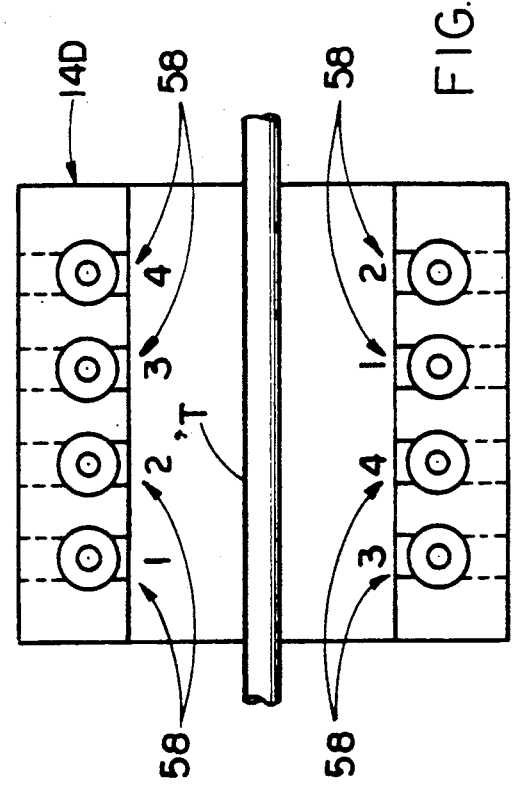
FIG. 66

ULTRASONIC TUBE INSPECTION STATION

CROSS REFERENCE TO RELATED APPLICATION

Reference is hereby made to the following copending patent application assigned to the same assignee as the present invention: "Rapid Changeover Multi-Diameter Ultrasonic Tube Inspection System" by Clarence D. John, Jr., assigned U.S. Ser. No. 07/555,866 and filed July 20, 1990.

BACKGROUND OF THE INVENTION

1. Field of the Invention

The present invention relates generally to tube quality inspection, and more particularly, to features of an ultrasonic tube inspection station which can advantageously be employed in a rapid changeover multi-diameter tube inspection system.

2. Description of the Prior Art

Because of their critical roles in fuel, control and instrumentation rods in nuclear reactors, tubes composed of zirconium and other materials must meet very stringent quality control standards. Parameters of interest are typically outside diameter, inside diameter, and wall thickness of the tube and material flaws in the tube. Ultrasonic inspection is one common method used to identify unacceptable dimensional deviations and material flaws in the tube.

These parameters of the tube are measured by ultrasonic transducers which send out ultrasound waves, pick up the echo of such waves and transform it into voltage signals which are recorded on a strip chart and visually tracked on a display, such as a cathode ray tube. These transducers, located in tanks filled with water, read the tube dimensions and flaws as a drive system feeds the tube through the tank. One conventional ultrasonic tube inspection system is disclosed in Furon et al. U.S. Pat. No. 3,828,609. One conventional tube drive apparatus is disclosed in Clarence D, John, Jr. U.S. Pat. No. 4,735,541 which is assigned to the assignee of the present invention.

The problem with conventional ultrasonic tube inspection systems is that in order to inspect tubes of different diameter sizes the orientation of the transducers in the tank must be changed, possibly every few hours or every week, depending on the need. The changeover time for converting the system to handle a different tube diameter size may typically take from four to eight hours.

Consequently, a need exists for improvements in ultrasonic tube inspection systems which will avoid the necessity to perform the time-consuming modifications previously required in order to inspect different sized tubes.

SUMMARY OF THE INVENTION

The present invention provides an ultrasonic tube inspection station for a rapid changeover multi-diameter tube inspection system which is designed to satisfy the aforementioned needs. The combinations of features of the tube inspection system which permit inspection of tubes with different diameter sizes and rapid changeover from inspection of one diameter size tube to inspection of another in a short period of time, compared to prior art inspection systems, comprise the invention claimed in the patent application cross-referenced above. The present invention relates to features of an ultrasonic tube inspection station which can be employed in the rapid changeover multi-diameter tube inspection system as well as in other inspection systems to provide further advantages in terms of improved adjustability of transducer assemblies and decrease in the overall size of the inspection systems.

Accordingly, the present invention relates to an inspection station which comprises (a) a receptacle having interconnected walls defining a cavity for holding energy coupling liquid and receiving an object to be inspected in the liquid, at least one wall having interior and exterior surfaces, a longitudinal bore defined between and spaced from the surfaces and extending within the one wall from an opening at the top of the one wall above the cavity, and a transverse bore extending through the one wall, the transverse bore intersecting with the longitudinal bore and open at both the interior and exterior surfaces of the one wall; (b) a transducer having first and second opposite ends, the transducer being operable for sending waves of energy from the first end of the one wall into the cavity toward the object and receiving echos of energy at the first end from the object for measuring a parameter of the object, the transducer having means at the second end for transmitting input and output signals to and from the transducer; and (c) mean removably mounted in the longitudinal and transverse bores of the one wall and removably mounting the transducer in the transverse bore of the one wall such that the first end of the transducer communicates with the cavity and the second end of the transducer communicates with the exterior of the receptacle.

The present invention also relates to a tube inspection system capable of rapid changeover for inspecting tubes of different diameters. The inspection system comprises: (a) a serial arrangement of multiple separate inspection stations corresponding to different orientations of tube flaws for different tube diameter sizes to be inspected; and (b) tube parameter measuring means supported at each of the stations in a predetermined configuration corresponding to the diameter size of the particular tube to be inspected at the respective station without the need for readjustment. The serial arrangement of inspection stations includes a separate tube dimension inspection station for inspecting tubes irrespective of their diameter sizes, a separate tube flaw inspection station for inspecting tubes of the different diameter sizes for transverse flaws, and a separate tube transverse flaw inspection station for inspecting tubes of the different diameter sizes for longitudinal flaws. The tube parameter measuring means at the separate transverse flaw inspection station includes separate transverse flaw inspecting transducer assemblies for inspecting tubes of the different diameter sizes. The tube parameter measuring means at the separate longitudinal flaw inspection station includes separate longitudinal flaw inspecting transducer assemblies for inspecting tubes of the different diameter sizes.

These and other features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the course of the following detailed description, reference will be made to the attached drawings in which:

FIG. 8 is an enlarged top plan view of a tube dimension inspection station of the tube inspection system of FIG. 3 in accordance with the present invention.

FIG. 9 is a side elevational view of the tube dimension inspection station as seen along line 9—9 of FIG. 8.

FIG. 10 is an end elevational view of the tube dimension inspection station as seen along 10—10 of FIG. 9.

FIG. 15 is an enlarged top plan view of one of the tube flaw inspection stations of the tube inspection system of FIG. 3 in accordance with the present invention.

FIG. 16 is a side elevational view of the tube flaw inspection station as seen along line 16—16 of FIG. 15.

FIG. 17 is an end elevational view of the tube flaw inspection station as seen along 17—17 of FIG. 16.

FIG. 22 is an enlarged fragmentary sectional view of the receptacle and one of the longitudinal flaw transducer assemblies of the arrangement of transducer assemblies of FIG. 19.

FIG. 23 is an enlarged side elevational view of a transducer mounting cylinder of the longitudinal flaw transducer assembly of FIG. 22 removed from the assembly.

FIG. 24 is an enlarged plan view of a retainer plate of the longitudinal flaw transducer assembly of FIG. 22 removed from the assembly.

FIG. 25 is an end view of the retainer plate as seen along line 25—25 of FIG. 24.

FIG. 34.

FIG. 40 is a horizontal sectional view of the inspection station taken along line 40—40 of FIG. 39.

FIG. 41 is an enlarged side elevational view of a mounting cylinder of the inspection station adjustable transducer assembly of FIG. 39 removed from the assembly.

FIG. 42 is an axial sectional view of the transducer mounting cylinder taken along line 42—42 of FIG. 41.

FIG. 43 is a fragmentary side elevational view of a tube flaw inspection station having another embodiment of an adjustable longitudinal or transverse flaw transducer assembly in accordance with the present invention.

FIG. 44 is a fragmentary vertical sectional view of the inspection station taken along line 44—44 of FIG. 43.

FIG. 45 is a fragmentary horizontal sectional view of the inspection station taken along line 45—45 of FIG. 43.

FIG. 46 is an end elevational view of a split spherical mounting bearing of the inspection station adjustable transducer assembly of FIG. 43 removed from the assembly.

FIG. 47 is a side elevational view of the split mounting bearing as seen along line 47—47 of FIG. 46.

FIG. 56 is a fragmentary side elevational view of a tube flaw inspection station having a further embodiment of an adjustable longitudinal flaw transducer assembly in accordance with the present invention.

FIG. 57 is a fragmentary vertical sectional view of the inspection station taken along line 57—57 of FIG. 56.

FIG. 58 is a view similar to that of FIG. 57 illustrating the range of horizontal swivel movement of a two-piece cylindrical mounting bearing of the adjustable transducer assembly.

FIG. 64 is a diagrammatic representation of one embodiment of the multiple transducer assemblies oriented for transverse flaw inspection of tubes having the different diameter sizes for use in the inspection system of FIG. 63.

FIG. 65 is a diagrammatic representation of another embodiment of the multiple transducer assemblies oriented for transverse flaw inspection of tubes having the different diameter sizes for use in the inspection system of FIG. 63.

FIG. 66 is a diagrammatic representation of the multiple transducer assemblies oriented for longitudinal flaw inspection of tubes having the different diameter sizes for use in the inspection system of FIG. 63.

DESCRIPTION OF THE PREFERRED EMBODIMENTS

Figure 1:
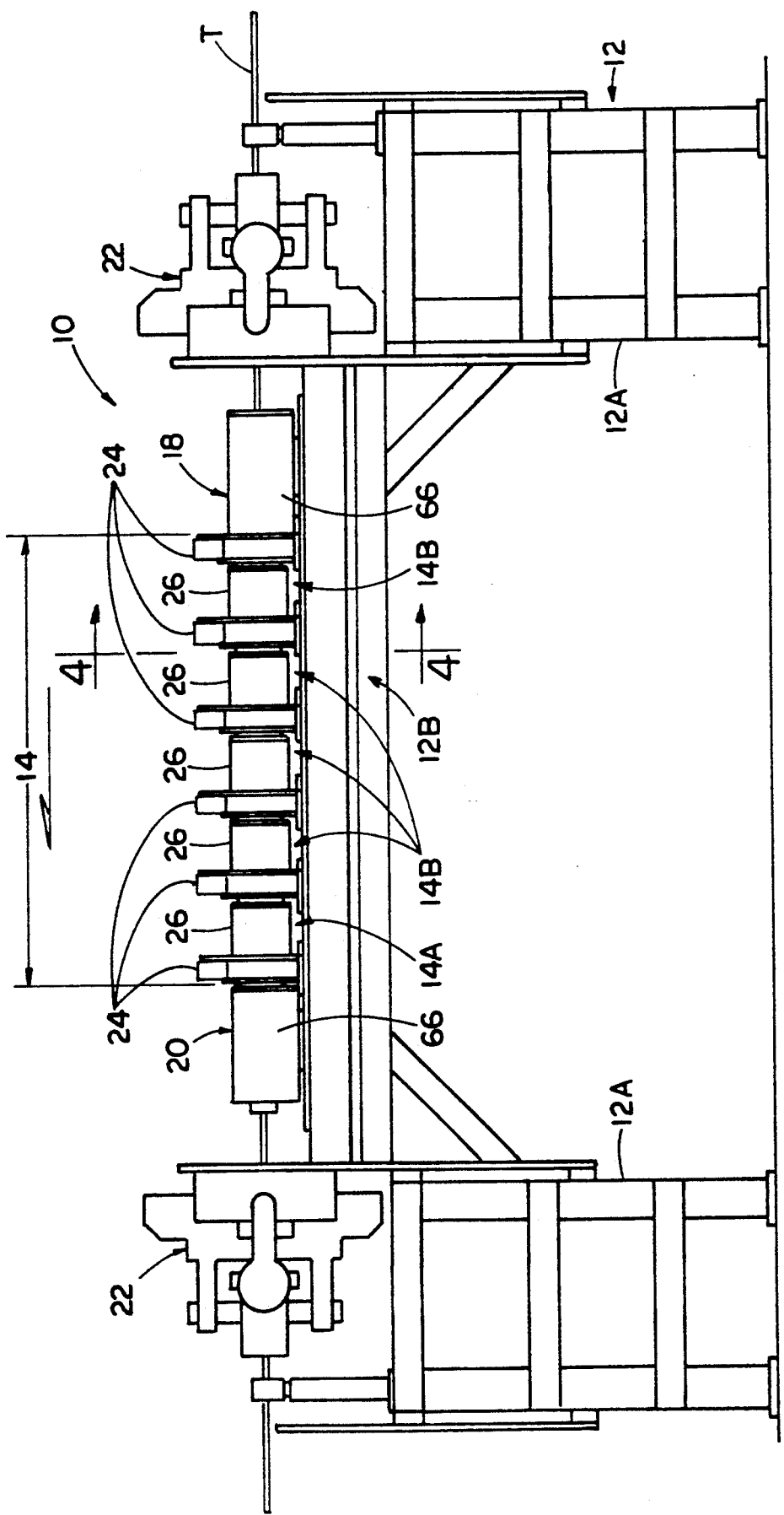
FIG. 1 is a side elevational view of a rapid changeover multi-diameter tube inspection system employing ultrasonic tube inspection stations which incorporate the features of the present invention.

In the following description, like reference characters designate like or corresponding parts throughout the several views of the drawings. Also in the following description, it is to be understood that such terms as "forward", "rearward", "left", "right", "upwardly", "downwardly", and the like are words of convenience and are not to be construed as limiting terms.

In General

Figure 3:
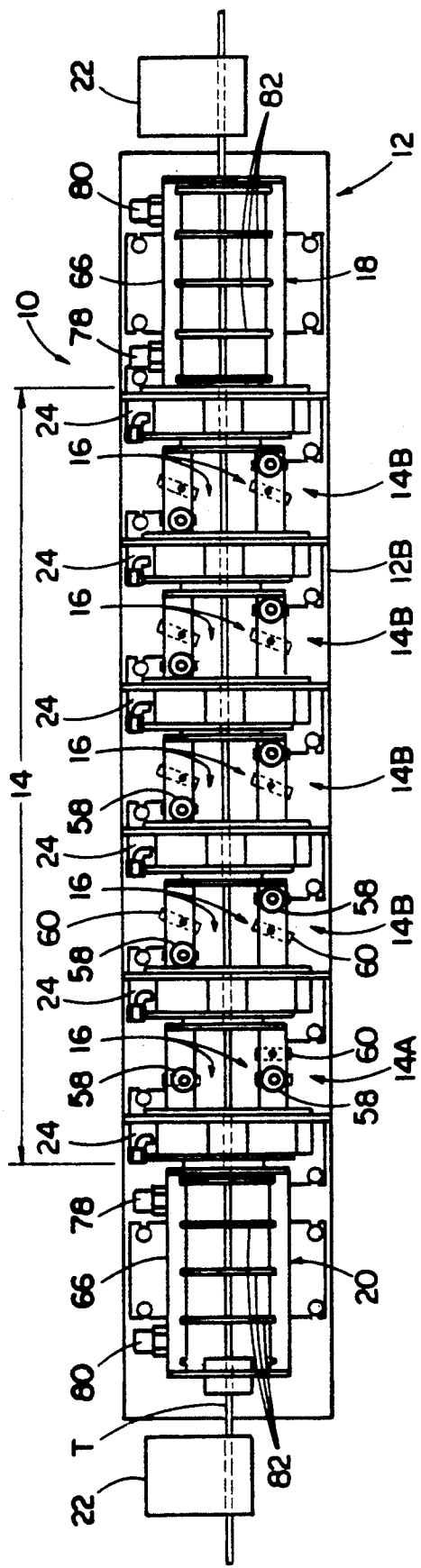
FIG. 3 is a top plan view of the tube inspection system as seen along line 3—3 of FIG. 2.
Figure 2:
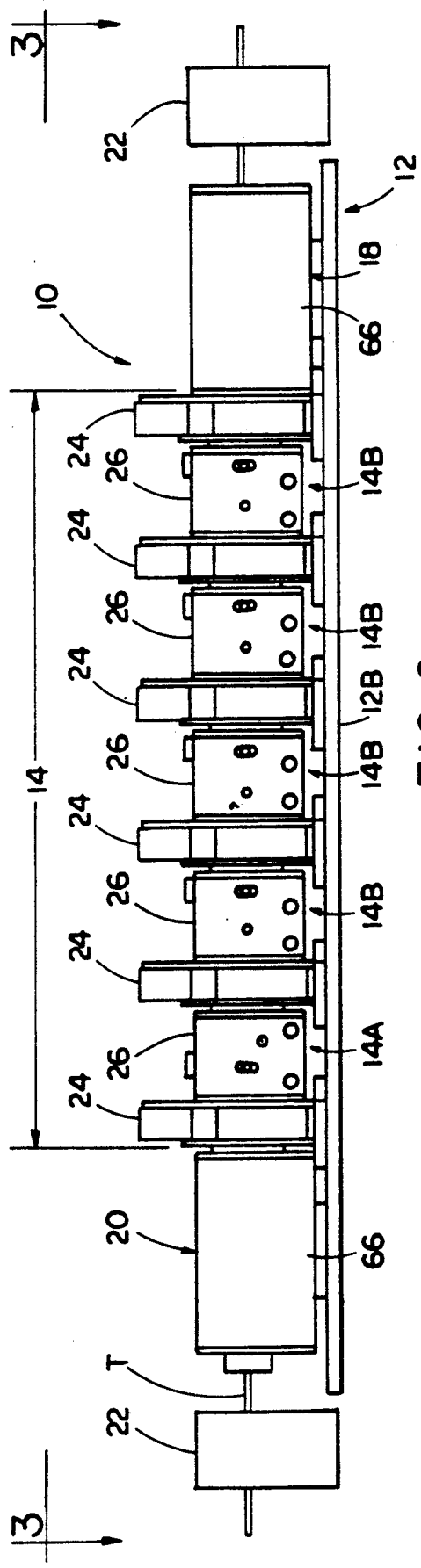
FIG. 2 is an enlarged fragmentary side elevational view of the tube inspection system of FIG. 1.
Figure 5:
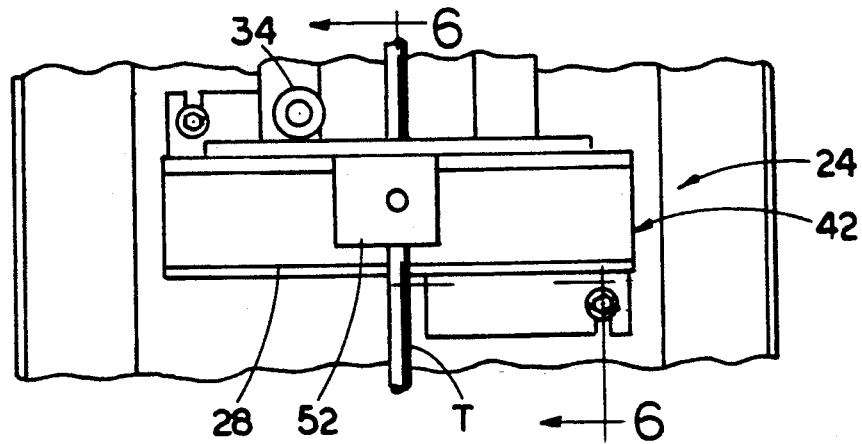
FIG. 5 is a top plan view of the tube guide stand as seen along line 5—5 of FIG. 4.

Referring to the drawings, and particularly to FIGS. 1 to 3, there is shown a rapid changeover multi-diameter tube inspection system, generally designated 10, whose overall combinations of features constitute the invention of the above cross-referenced patent application. The multi-diameter tube inspection system 10 can be used to ultrasonically inspect tubes of different diameter sizes intended to be employed in many different uses. One particular application of interest is the inspection of tubes T to be used in fuel, instrumentation, and control rods of a nuclear fuel assembly.

In its basic components, the multi-diameter tube inspection system 10 includes a support framework 12, a serial arrangement 14 of multiple separate inspection stations 14A, 14B, tube parameter measuring means 16, entry and exit liquid level control stations 18, 20 and tube drives 22. Certain features of the inspection stations 14A, 14B constitute the present invention and will be described in detail below.

The support framework 12 of the inspection system 10 includes a pair of spaced apart upright opposite end frame portions 12A and a middle frame portion 12B extending horizontally between and interconnecting the end frame portions 12A. The horizontal middle frame portion 12B supports the serial arrangement 14 of inspection stations 14A, 14B and the entry and exit liquid level control stations 18 and 20. The opposite end frame portions 12A respectively support the tube drives 22 adjacent the respective liquid level control stations 18, 20 at the opposite ends of the serial arrangement 14 of inspection stations 14A, 14B.

The separate inspection stations 14A, 14B in the serial arrangement 14 thereof correspond to the tube dimensions and different tube diameter sizes to be inspected. In particular, the stations are composed of a single tube dimension station 14A and a plurality of tube flaw inspection stations 14B.

Serial Arrangement of Separate Inspection Stations

Referring to FIGS. 1 to 21, each of the inspection stations 14A, 14B in the serial arrangement 14 thereof includes a tube guide stand 24 and a receptacle 26. As best seen in FIGS. 4 to 7, the tube guide stand 24 includes a housing 28 which supports from one end thereof the one receptacle 26 of the same respective inspection station. The housing 28 has a base 30 slidably mounted to the horizontal middle frame portion 12B by a dovetail interconnection 32. The housing 28 and receptacle 26 therewith can be slidably moved to a desired position along the frame portion 12B via the dovetail interconnection 32 and then anchored at such position by tightening a plurality of fasteners 34. A centering rod 36 attached to the housing base 30 slides in a complementary recess 38 formed in the middle frame portion 12B to maintain all of the tube guide stands 24 in alignment so as to define a common centerline C.

Figure 4:
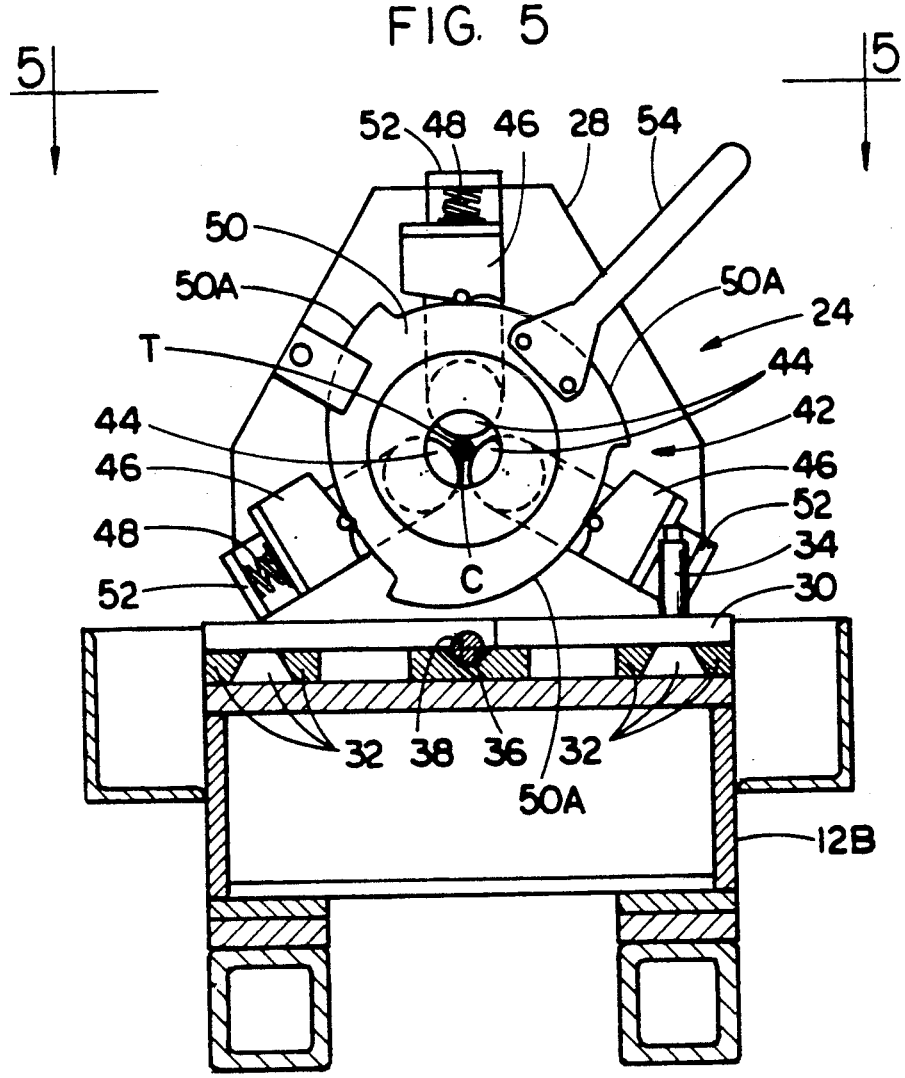
FIG. 4 is an enlarged end elevational view of one of the tube guide stands of the tube inspection system taken along line 4—4 of FIG. 1.
Figures 6, 7:
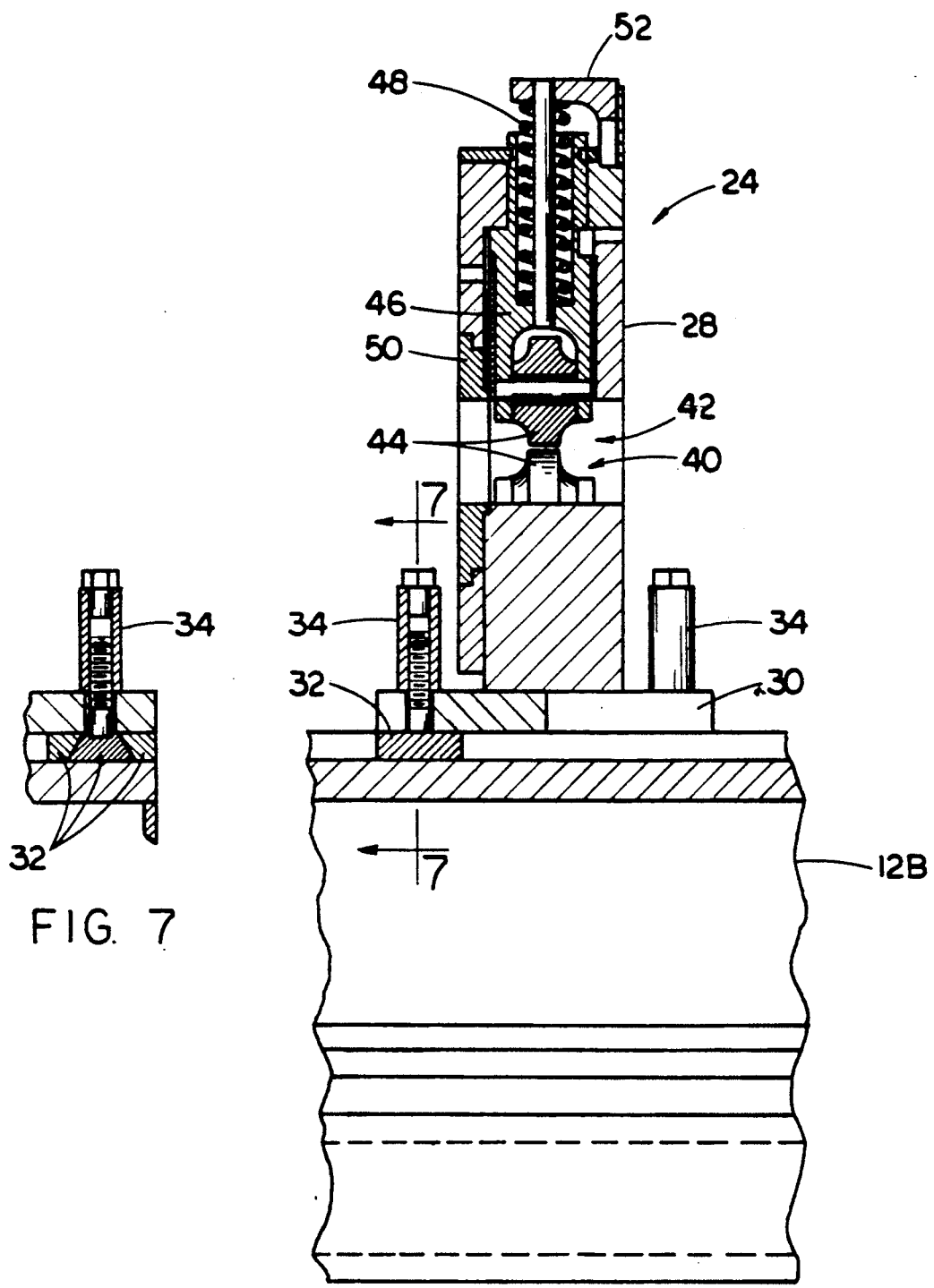
FIG. 6 is a cross-sectional view of the tube guide stand taken along line 6—6 of FIG. 5.
FIG. 7 is a fragmentary axial sectional view taken along line 7—7 of FIG. 6.
Figure 11:
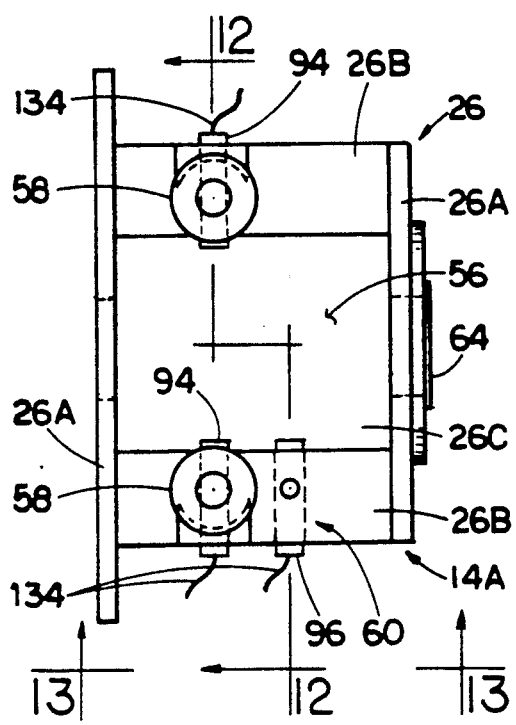
FIG. 11 is an enlarged top plan view of a receptacle and an arrangement of ultrasonic transducer assemblies of the tube dimension inspection station of FIG. 8.

As best seen in FIGS. 4 and 6, each housing 28 has a central passage 40 for receiving and passing a tube T therethrough. A self-centering mechanism 42 is mounted on the housing 28 and aligned with the passage 40. The self-centering mechanism 42 is operable for guiding the tube T through the passage 40 along the common centerline C irrespective of which tube diameter size is being inspected. Thus, together the self-centering mechanisms 42 of the aligned tube guide stands 24 ensure that each tube T is guided through the inspection stations 14A, 14B centered coaxially along the common centerline C.

More particularly, the self-centering mechanism 42 includes a plurality of tube support elements in the form of rollers 44, a plurality of arms 46 mounted to the housing 28 for movement in a reciprocal radial relation to the common centerline C and mounted in spaced relation to one another circumferentially about the common centerline C. Each arm 46 mounts one of the tube support rollers 44 at its inner end such that the rollers 44 are arranged in spaced circumferential relation about the tube T for maintaining the tube aligned along and coaxially with the common centerline C.

The self-centering mechanism 42 also includes positioning means in the form of a plurality of biasing springs 48 and a disk- or plate-like actuating cam 50. Each biasing spring 48 is mounted between a stationary bracket 52 attached to the housing 28 and an outer end of one of the arms 46 and acts to bias the arm to move radially inwardly toward the common centerline C so as to maintain the tube support rollers 44 in engagement with the tube T. The actuating cam 50 is rotatably mounted to the housing 28 and has a plurality of circumferentially-spaced peripheral cam surfaces 50A each engaged with one of the arms 46. Rotation of the cam 50 revolves its cam surfaces 50A and concurrently radially moves the arms 46 outwardly or permits the arms to be moved inwardly by the springs 48 and concurrently move tube support rollers 44 away from or toward the tube T to adjust their radial positions to accommodate any diameter size tube coaxially along the common centerline C. A lever 54 is attached to the cam 50 for use in manually rotatably moving the cam.

Referring now to FIGS. 8 to 21, each of the receptacles 26 of the dimension and flaw inspection stations 14A, 14B is formed by interconnected pairs of end walls 26A and side walls 26B and a bottom wall 26C and is open at the top. The interconnected walls of the receptacle 26 define a cavity 56 capable of holding a quantity of an energy coupling liquid, such as water. As will be described in detail later, the side walls 26B of the receptacle 26 mounts the tube parameter measuring means 16 which preferably are in the form of first and second ultrasonic transducer assemblies 58, 60. The end walls 26A of the receptacle 26 have a pair of opposite openings 62 which communicate with the cavity 56 for receiving and passing the tube T therethrough such that the various tube parameters of interest can be measured by the transducer assemblies 58, 60 as the tube passes through the cavity 56 and the coupling liquid contained therein.

The cavities 56 of the respective receptacles 26 are interconnected to one another at the openings 62 in the end walls 26A of the receptacles 26 by the central passages 40 of the tube guide stand housings 28 so as to permit the tube T to pass through the serial arrangement 14 of inspection stations 14A, 14B along the common centerline C. Annular seals 64, such as O-rings, are provided about the openings 62 and between the tube guide stand 24 of one inspection station and the receptacle 26 of the next adjacent inspection station to inhibit leakage of coupling liquid from between the stations. The interconnection between the inspection stations 14A, 14B which permits passage of the tube also permits communication of some of the coupling liquid from one receptacle 26 to the next. For proper operation of the transducer assemblies 58, 60, the coupling liquid is required to be maintained at a certain minimum level in the receptacle cavities 56. The entry and exit liquid level control stations 18, 20 are operable to ensure fulfillment of this requirement.

Liquid Level Control Stations

Referring to FIGS. 26 to 37, the entry and exit liquid level control stations 18, 20 are disposed at the respective opposite ends of the serial arrangement 14 of inspection stations 14A, 14B. As briefly mentioned above, the control stations 18, 20 are operable for controlling the levels of energy coupling liquid, such as water, in the receptacle cavities 56 of the inspection stations 14A, 14B to ensure that the liquid levels remain above the minimum required for effective operation of the transducer assemblies 58, 60.

More particularly, each of the liquid level control stations 18, 20 includes a tank 66 and a liquid level regulating arrangement 68 coupled to each tank 66 for controlling the level of liquid therein and thereby in the receptacle cavities 56 of the inspection stations 14A, 14B. Each tank 66 is disposed at one of the opposite ends of the serial arrangement 14 of inspection stations 14A, 14B and interconnected in fluid flow communication with the respective inspection station at the one opposite end. Specifically, the entry liquid level control station 18 is interconnected to the first dimension inspection stations 14A via an additional tube guide stand 24A, as seen in FIGS. 1 to 3, 26 and 27. Also, each tank 66 has a chamber 70 for holding energy coupling liquid, such as water, and a pair of opposite inlet and outlet openings 72, 74 to the chamber 70 to permit passage of the tube T through the chamber.

Each liquid level regulating arrangement 68 of the control stations 18, 20 includes a plurality of dam and guide assemblies 76 mounted in the tank 66 and a pair of liquid inlet and outlet orifices 78, 80 on the tank 66 which communicate between the tank chamber 70 and an external water supply and drain. Each dam and guide assembly 76 is composed of a plate-like dam member 82 and a tube guide member 84. The dam member 82 has a recessed portion 82A along the middle of its upper edge providing a liquid overflow weir. The tube guide member 84 is composed of an annular bushing 86 mounted in a central opening 88 of the dam member 82 and an annular collar 90 attached to the dam member 82 adjacent the opening 88 for holding the bushing 86 in the opening 88. Bushings 86 of different opening sizes are provided and changed to accommodate different diameter sizes of tubes inspected. Alternative different dam members 82 can be provided matched with different tube diameter sizes so that changeover is accomplished merely by lifting out and replacing the dam members.

The interior surfaces of the bottom and sides of the tanks 66 have spaced grooves 92 defined therein which receive and support the plate-like dam members 82 in upright orientations so as to define a succession of liquid holding sections 70A, 70B, 70C, 70D of the tank chamber 70. The level of liquid in the outboard chamber section 70D communicates directly with the outlet orifice 80 and thus has a much lower level of liquid than in the other chamber sections 70A, 70B, 70C. Liquid flows from the inlet orifice 78 directly into the inboard chamber section 70A and then over the upper overflow portions 82A of the dam members 82 and through the intermediate chamber sections 70B, 70C to the outboard chamber section 70D. In such manner the liquid is maintained in the chamber sections 70A, 70B, 70C and thereby in the receptacles 26 at a more or less constant level above the minimum level required.

Tube Drives

As seen generally in FIGS. 1 to 3, the tube drives 22 are disposed adjacent to and outboard of the entry and exit liquid level control stations 18, 20 at the opposite ends of the serial arrangement 14 of inspection stations 14A, 14B. The tube drives 22 are operable for driving tubes T through the inspection and level control stations and, together with the tube guide stands 24, maintain the tube in coaxial alignment along the common centerline C irrespective of which tube diameter size is being inspected. The tube drives 22 are spaced from one another through a distance less than the length of the tube being inspected so that at least one of the drives 22 is engaged with the tube at all times.

The construction of each of the tube drives 22 preferably is substantially the same as the one disclosed in Clarence D. John, Jr. U.S. Pat. No. 4,735,541, assigned to the same assignee as the present invention. The disclosure of that patent is incorporated herein by reference, and to obtain a greater understanding of the details of the tube drives 22, attention is directed to that patent.

Tube Parameter Measuring Means

Referring now to FIGS. 8 to 25, the tube parameter measuring means 16 in the form of first and second ultrasonic transducer assemblies 58, 60 are associated with the receptacle 26 of each of the inspection stations 14A, 14B. The transducer assemblies 58, 60 are supported in the proper predetermined orientation which matches the respective diameter size of the particular tube to be inspected at the respective inspection station. The provision of different ultrasonic transducer assemblies 58, 60 for different tube diameter sizes avoids the need for carrying out time-consuming readjustments whenever the diameter size of the tube being inspected is changed. All that the operator is required to do with respect to the changeover of transducer assemblies is to switch out, or electrically disconnect, the transducer assemblies which match the diameter sizes of tubes not being inspected and to switch in, or electrically connect, the transducer assemblies which match the diameter size of the tubes to be inspected next.

The first and second transducer assemblies 58, 60 each includes an ultrasonic transducer 94, 96 operable for sending out ultrasound waves and picking up the echo of such waves. At the tube dimension inspection station 14A, the pair of transducers 94 of the first transducer assemblies 58 respectively read the tube diameter and wall thickness, whereas the single transducer 96 of the second transducer assembly 60 is for calibration purposes. At each of the tube flaw inspection stations 14B, the pair of transducers 94 of the first transducer assemblies 58 respectively inspect for longitudinal flaws which typically take the form of lengthwise scratches found on the inside diameter surface of the tube. The transducers 94 are oriented to point in orthogonal relation to the tube but offset from the centerline of the tube, at an angle of incidence either above or below the centerline C. The pair of transducers 96 of the second transducer assemblies 60 respectively inspect for transverse flaws which typically take the form of circumferential scratches found on the outside diameter surface of the tube. The transducers 96 are oriented to point at small acute angles to the tube toward the centerline of the tube.

In accordance with the present invention, the first and second transducer assemblies 58, 60 are mounted to the side walls 26B of the receptacles 26 at the inspection stations 14A, 14B. The side walls 26B have first and second pairs 98, 100 of interconnected transverse and longitudinal bores 102, 104 and 106, 108 for respectively receiving the transducers 94, 96 nd mounting members 110, 112 of the first and second transducer assemblies 58, 60. The mounting members 110, 112 either mount the transducers or hold them in the desired orientation. The transverse bores 102, 106 of the first and second pairs 98, 100, which receive the transducers 94, 96, extend between and open at the interior and exterior surfaces of the side walls 26B. The longitudinal bores 104, 108 of the first and second pairs 98, 100, which receive the mounting members 110, 112, extend vertically within the side walls 26B and open at the upper surface of the side walls and into the respective transverse bores 102, 106.

Referring to FIGS. 9, 12, 13, 19 and 20, the transverse bores 102, which receive the transducers 94 of the first transducer assemblies 58 that inspect for longitudinal flaws, are oblong in cross sectional shape to permit vertical adjustment of the transducers 94 to the desired position either above or below the centerline of the tube. On the other hand, the tranverse bores 106, which receive the transducers 96 of the second transducer assemblies 60 that inspect for transverse flaws, are substantially the same cylindrical shape as the transducers 96 and are formed through the side walls 26B so as to be in the desired alignment with the centerline C and thereby with the tube extending through the receptacles 26 of the inspection stations 14B. Therefore, adjustment of the transducers 96 is neither required nor permitted.

Referring to FIGS. 12, 19, 22 and 23, the mounting members 110 of the first transducer assemblies 58 each include a mounting cylinder 114 having a transverse opening 116 for insertion of the transducer 94 and a central passage 118 leading from the upper side of the opening 116 to the upper end of the cylinder 114. The cylinder 114 is externally threaded at its upper end portion 114A and its central passage 118 is internally threaded at the lower end 118A. Also, the externally threaded upper end portion 114A of the cylinder 114 is reduced in outside diameter to provide an annulus 120 between the inside diameter of the longitudinal bore 104 in the receptacle side wall 26B and the outside diameter of the externally threaded upper portion 114A of the mounting cylinder 114.

Referring to FIGS. 12, 19 and 22 to 25, the mounting members 110 of the first transducer assemblies 58 also include main set screws 122, internally-threaded end caps 124, assist spring 125, retainer plate 126, and auxiliary set screws 128. Each main set screw 122 threads into the internally threaded lower end 118A of the central passage 118 of the one mounting cylinder 114 and engages the transducer 94 to retain it in the transverse opening 116 of the mounting cylinder 114. Each end cap 124 is threaded on the externally-threaded upper end portion 114A of the mounting cylinder 114 and extends into the annulus 120. Rotation of the end cap 124 produces axial movement of the mounting cylinder 114 within the longitudinal bore 104 to position the transducer 94 within the transverse bore 102. Spring 125 located between the bottom of the longitudinal bore 104 and the bottom of the mounting cylinder 114 assists in repositioning of the cylinder 114 upon rotation of the end cap 124. The end cap 124 has a peripheral groove 130 into which the edge of the retainer plate 126 extends. When adjustment of the end cap 124 is accomplished, the retainer plate 126 is tightened by screws 132 to the top surface of the receptacle side wall 26B so as to clamp and hold the end cap 124 in a stationary position against further rotation. The auxiliary set screws 128 are threaded through the side wall 26B from the exterior thereof to further engage and hold the mounting cylinder 114 against inadvertent rotation.

Figure 12:
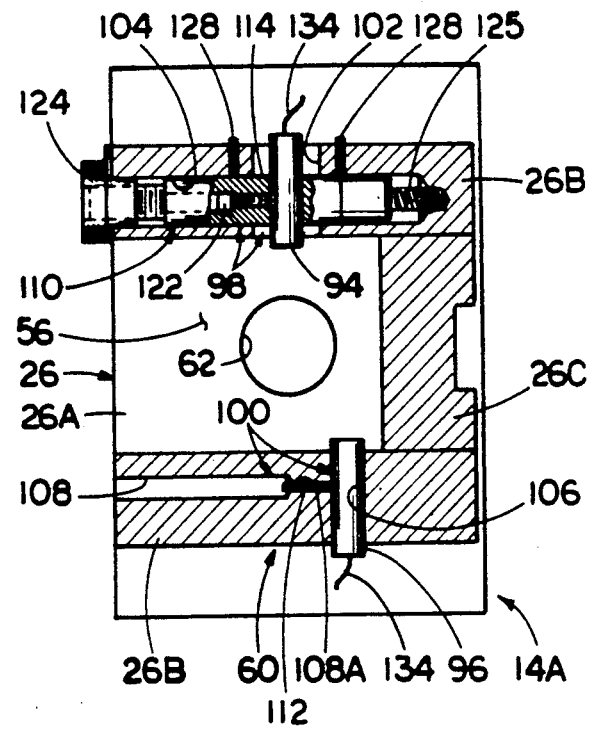
FIG. 12 is a cross sectional view of the receptacle and arrangement of transducer assemblies taken along line 12—12 of FIG. 11.
Figure 13:
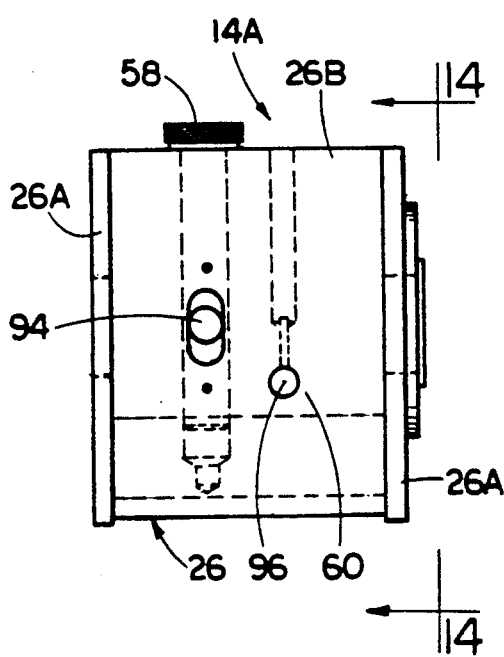
FIG. 13 is a side elevational view of the receptacle and arrangement of transducer assemblies as seen along line 13—13 of FIG. 11.
Figure 14:
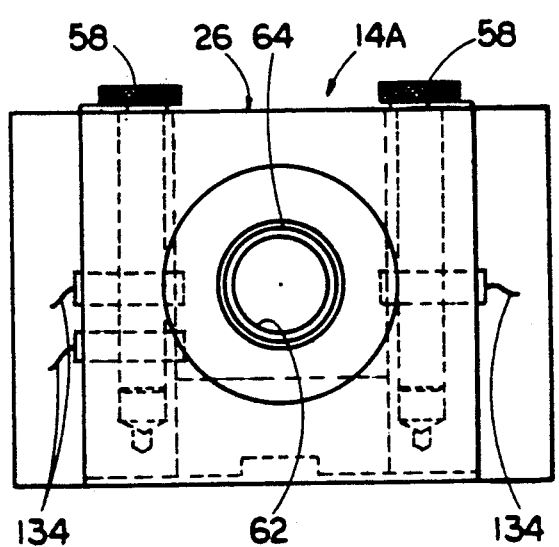
FIG. 14 is an end elevational view of the receptacle and arrangement of transducer assemblies as seen along line 14—14 of FIG. 13.
Figure 18:
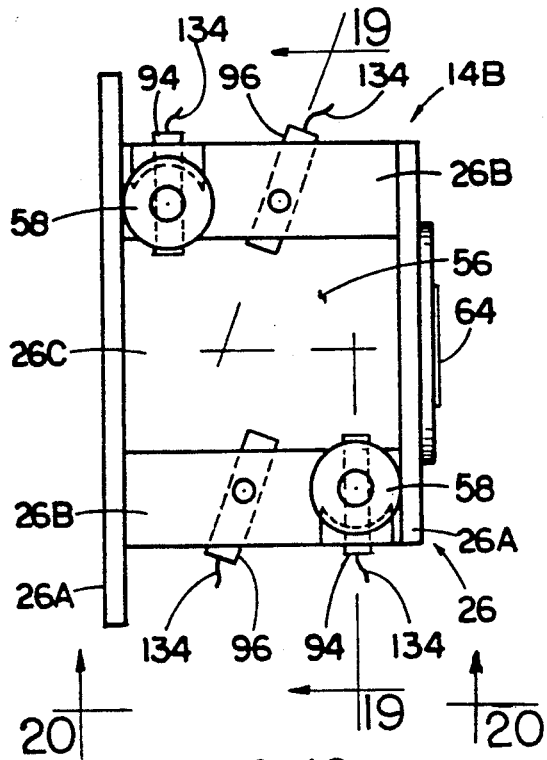
FIG. 18 is an enlarged top plan view of a receptacle and an arrangement of ultrasonic transducer assemblies of the tube flaw inspection station of FIG. 15.
Figure 19:
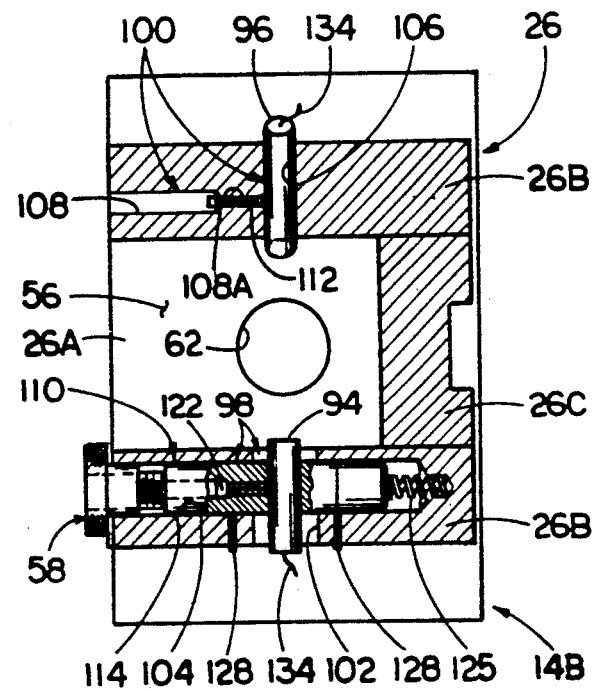
FIG. 19 is a cross sectional view of the receptacle and arrangement of transducer assemblies taken along line 19—19 of FIG. 18.
Figure 20:
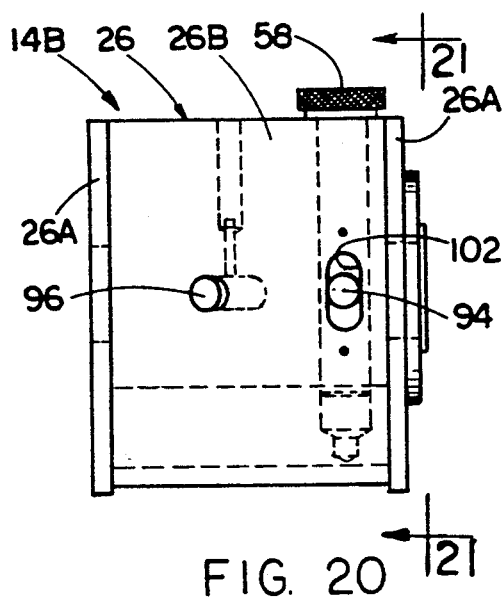
FIG. 20 is a side elevational view of the receptacle and arrangement of transducer assemblies as seen along line 20—20 of FIG. 18.
Figure 21:
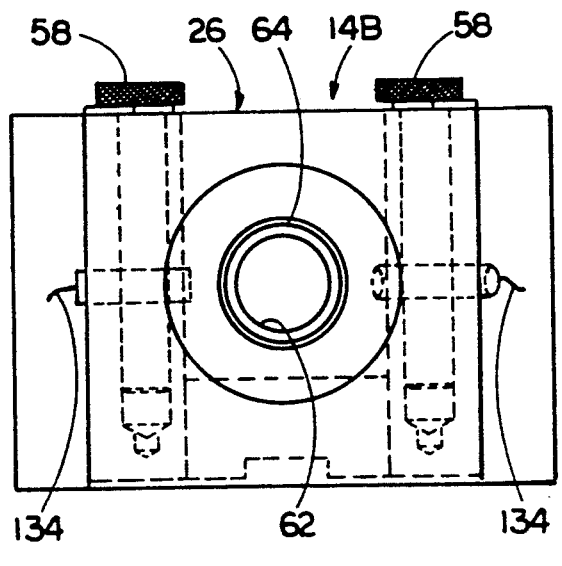
FIG. 21 is an end elevational view of the receptacle and arrangement of transducer assemblies as seen along line 21—21 of FIG. 20.
Figure 26:
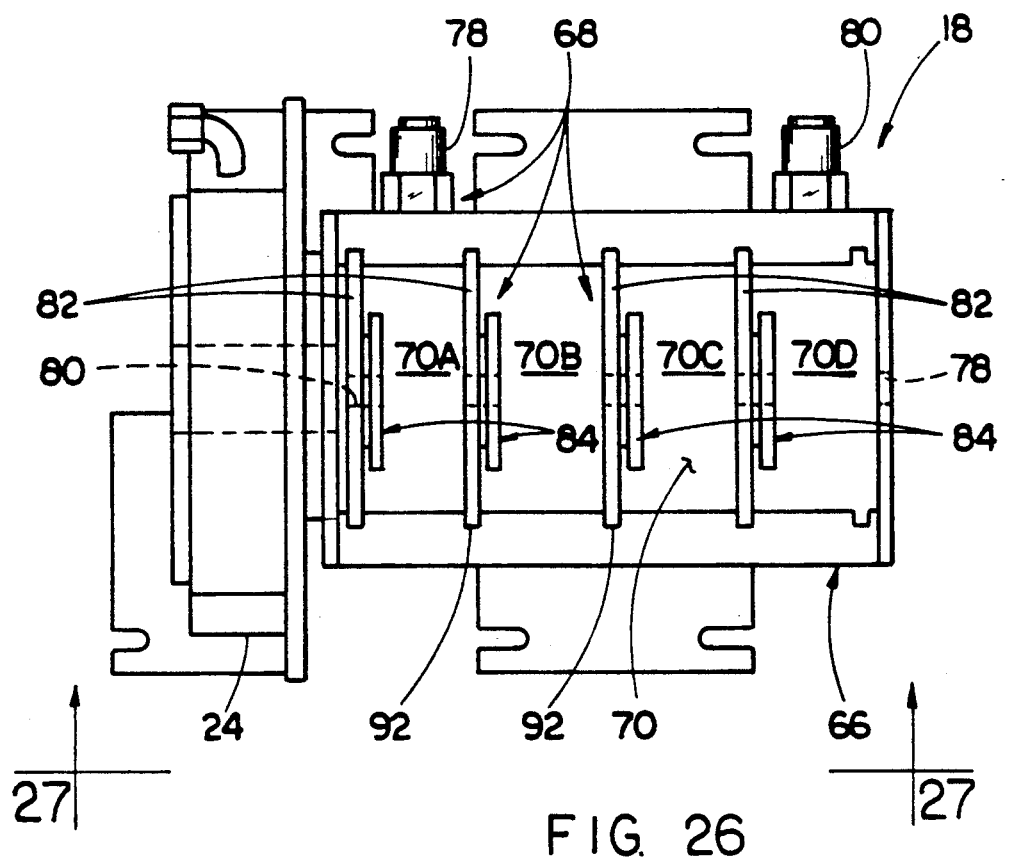
FIG. 26 is an enlarged top plan view of the entry liquid level control station and one of the tube guide stands of the tube inspection system.
Figure 27:
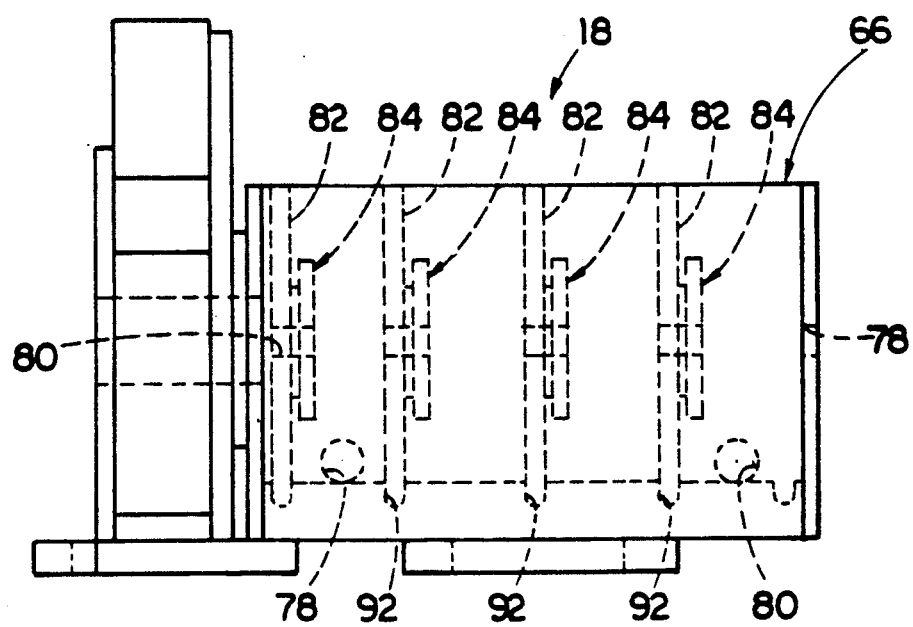
FIG. 27 is a side elevational view of the entry liquid level control station and one tube guide stand as seen along line 27—27 of FIG. 26.
Figure 28:
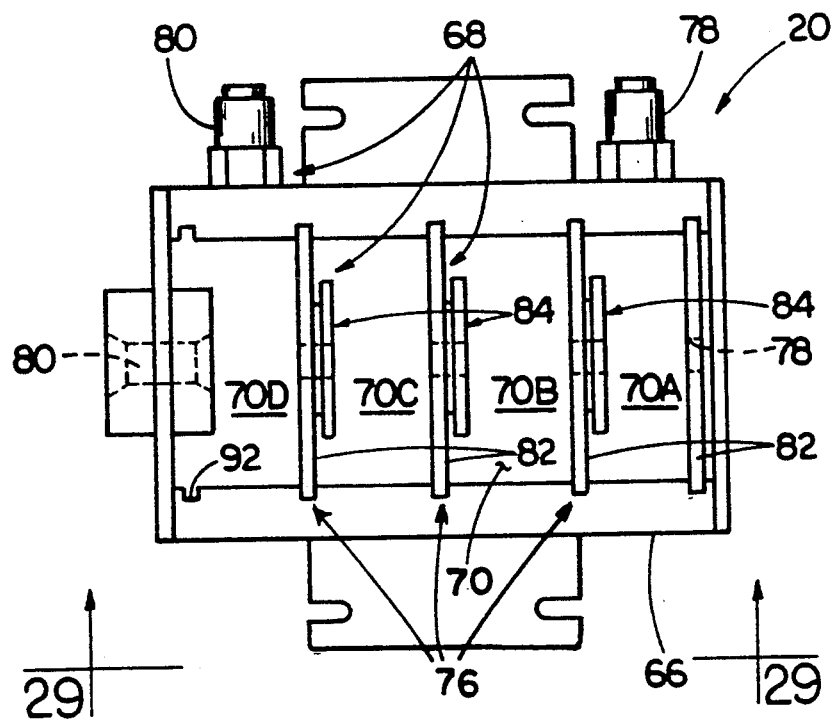
FIG. 28 is an enlarged top plan view of the exit liquid level control station of the tube inspection system.
Figure 29:
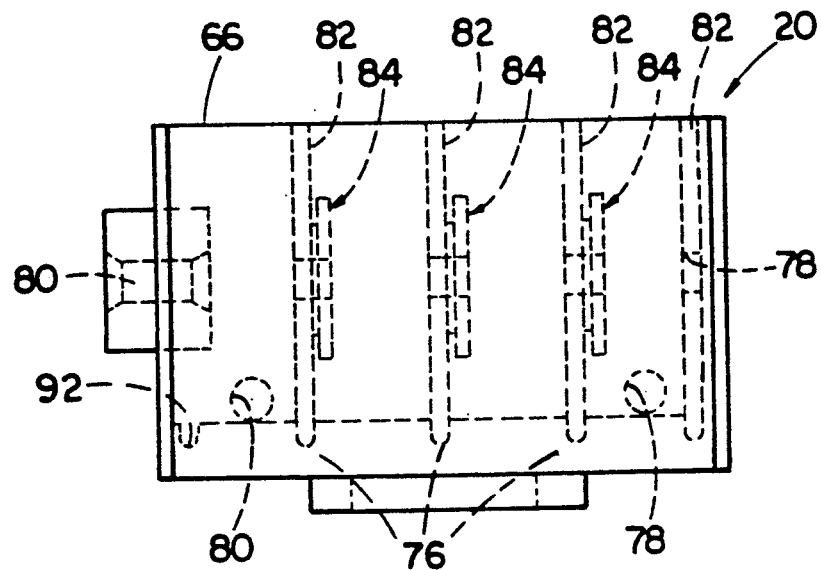
FIG. 29 is a side elevational view of the exit liquid level control station of the tube inspection system as seen along line 29—29 of FIG. 28.
Figure 35:
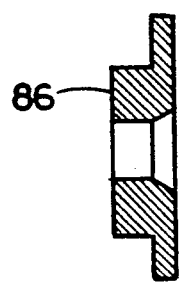
FIG. 35 is a cross-sectional view of the bushing taken along line 35—35 of FIG.
Figure 34:
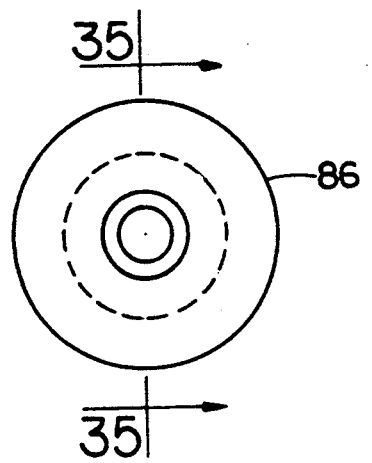
FIG. 34 is an enlarged side elevational view of a bushing of the dam and guide assembly of FIG. 31.
Figure 31:
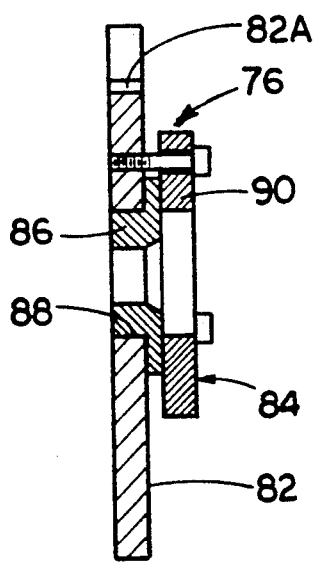
FIG. 31 is a cross-sectional view of the dam and guide assembly taken along line 31—31 of FIG. 30.
Figure 30:
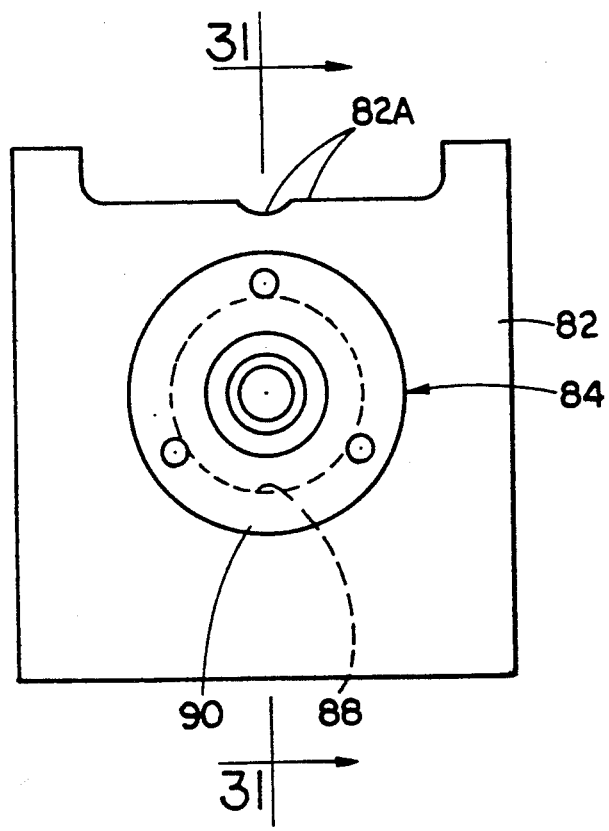
FIG. 30 is an end elevational view of one of a plurality of dam and guide assemblies composed of one dam member and one tube guide member and employed by the entry and exit liquid level control stations of FIGS. 26 and 28.
Figure 33:
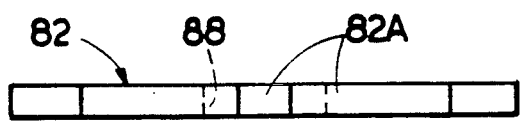
FIG. 33 is a top plan view of the dam member as seen along line 33—33 of FIG. 32.
Figure 32:
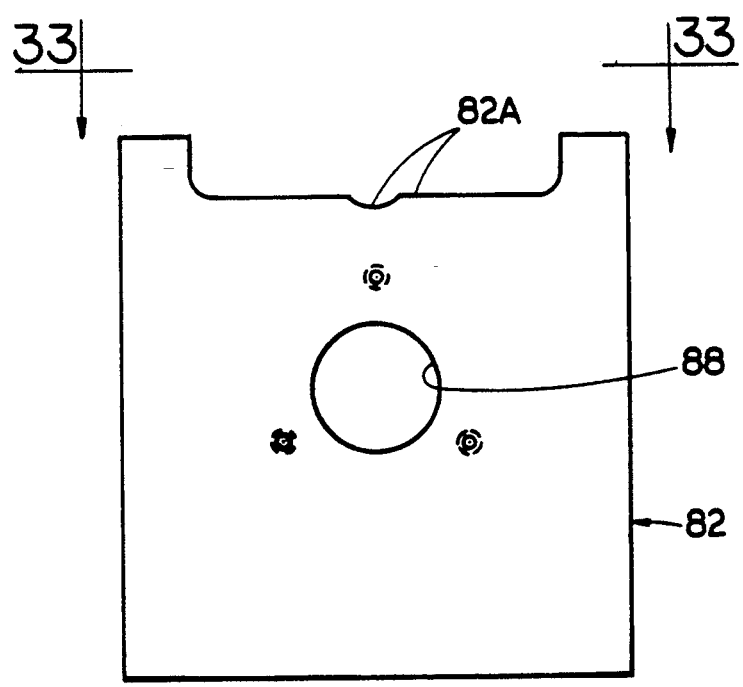
FIG. 32 is an end elevational view of one of a plurality of dam members employed by the entry and exit liquid level control stations of FIGS. 26 and 28.
Figures 36, 37:
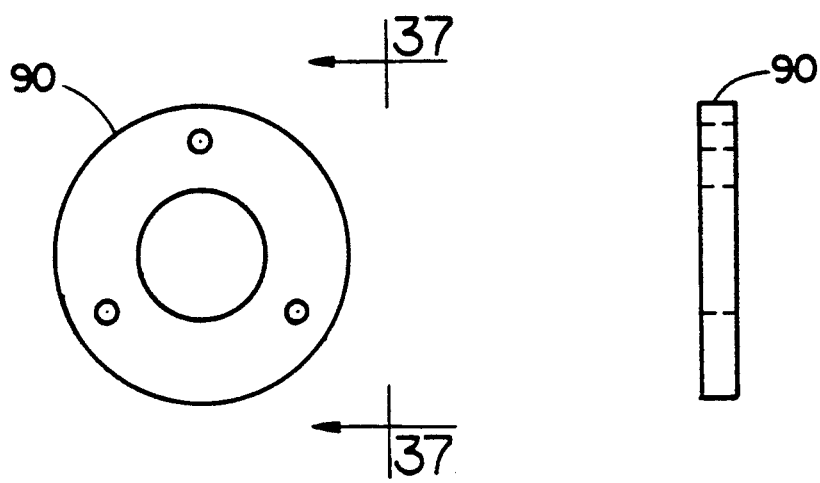
FIG. 36 is a side elevational view of a collar of the dam and guide assembly of FIG. 31.
FIG. 37 is an end elevational view of the collar as seen along line 37—37 of FIG. 36.

As readily apparent in FIGS. 12 and 19, the construction of the mounting members 112 of the second transducer assemblies 60 for anchoring the transducers 96 in place is much simpler than in the case of mounting members 110 of the first transducer assemblies 58 for the transducers 94, as just described above. The mounting members 112 merely are set screws which thread into the lower ends 108A of the longitudinal bores 108 and engage the transducers 96. Furthermore, it is readily apparent in FIGS. 11, 12, 14, 18, 19 and 21 that by the transverse bores 102, 106 being open at the exterior surfaces of the receptacle side walls 26B, signal conductors 134 are easily attached to transducers 94, 96 without contacting the liquid in the receptacles.

Modified Constructions of Tube Parameter Measuring Means

FIGS. 38 to 61 illustrate alternative embodiments of the tube parameter measuring means that can be used in the inspection stations in place of the ones described above to provide greater versatility in setup of transducer alignment relative to the tube T. The alternative embodiments as a group provide swivel movements in at least two orthogonal planes with most alternative embodiments being capable of undergoing universal swivel movements. These embodiments provide the operator or technician with the means to overcome defects inherent in transducers, such as a non-concentric beam, and thereby to compensate for idiosyncrasies in the setup alignment of the beam emanating from the transducers by providing adjustable mounting members permitting the above-mentioned swivel movements. The swivel mounting arrangement will permit the adjustment and optimization of the angle of incidence and reflection with the tube.

Figure 38:
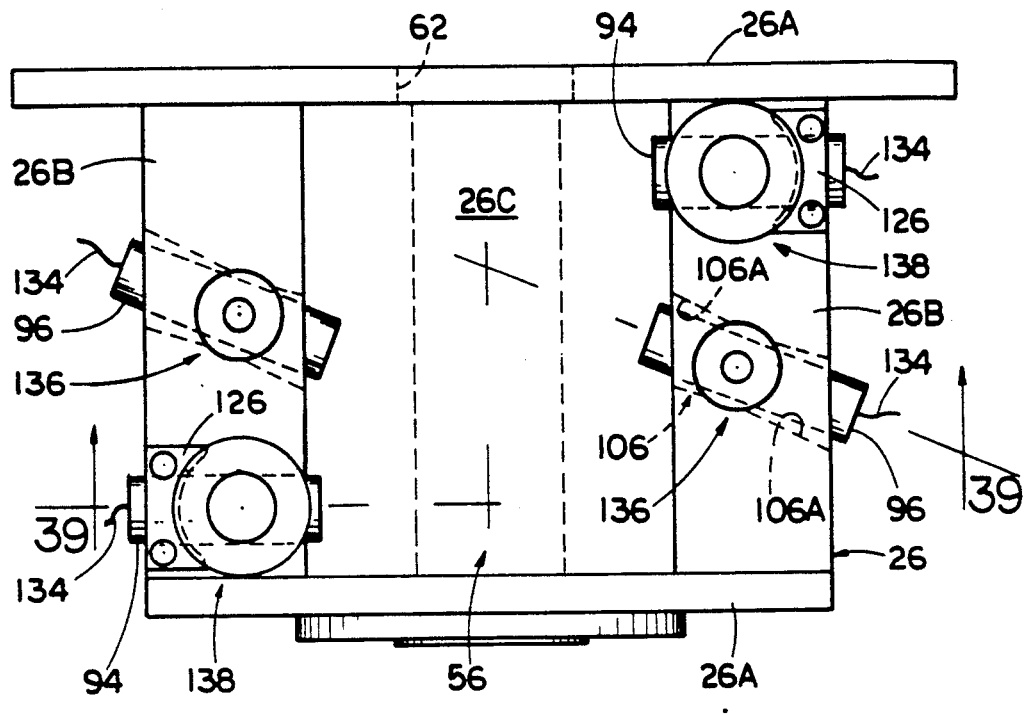
FIG. 38 is a top plan view of a tube flaw inspection station having one embodiment of an adjustable transverse flaw transducer assembly in accordance with the present invention.
Figure 39:
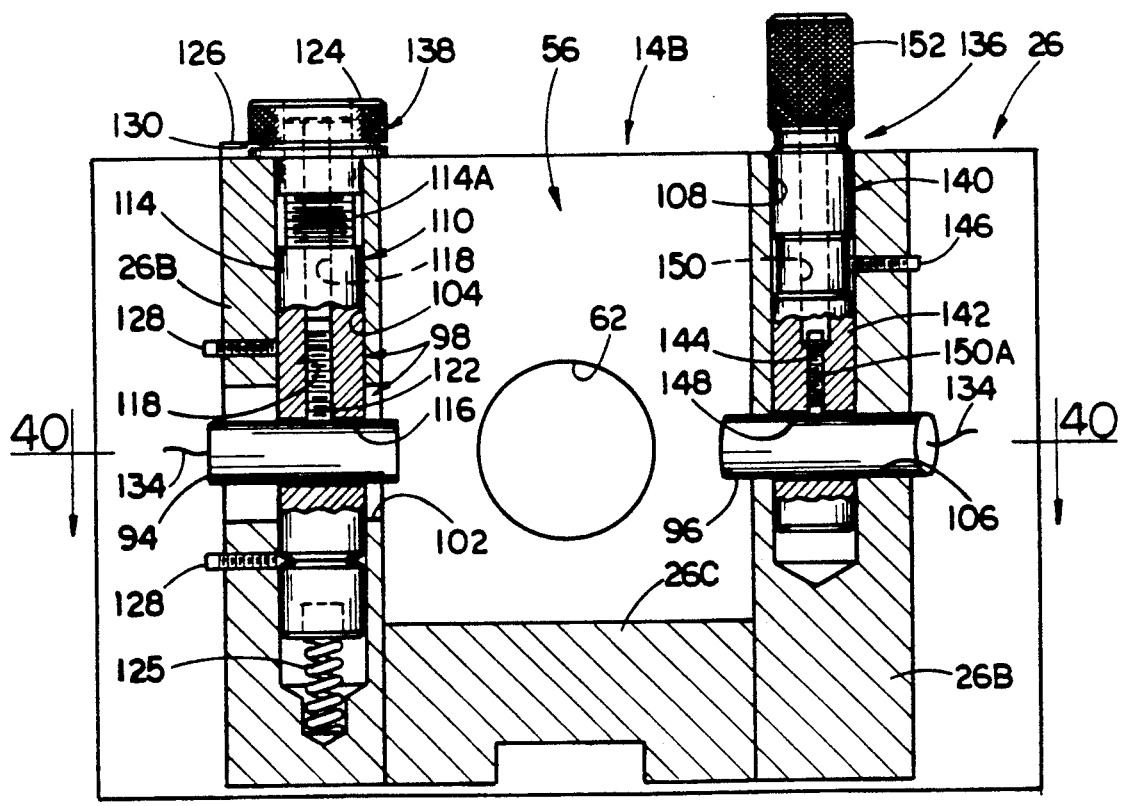
FIG. 39 is a vertical sectional view of the inspection station taken along line 39—39 of FIG. 38.

Referring first to FIGS. 38 to 42, a first alternative embodiment of the tube parameter measuring means 16 is an adjustable transverse flaw transducer assembly 136. The longitudinal flaw transducer assembly 138 is substantially identical to the transducer assembly 58 of FIG. 19 previously described. The adjustable transducer assembly 136 includes the transducer 96 and a mounting member 140. The mounting member 140 includes a mounting cylinder 142 and set screws 144, 146. The mounting cylinder 142 has a transverse opening 148 for insertion of the transducer 96 and a central passage 150 leading from the upper side of the opening 148 to the upper end of the cylinder 142. The cylinder 142 has a knob 152 which projects from the longitudinal bore 108 and is used for rotating the cylinder 142. The lower end 150A of the central passage 150 of the cylinder 142 is internally threaded for receiving the set screw 144 to engage and hold the transducer 96 at the desired position. The other set screw 146 is threaded through the side wall 26B and engages the mounting cylinder 142 to retain it at the desired angular position and prevent further rotation. As best seen in FIG. 38, the transverse bore 106 has dual conical portions 106A flaring in opposite directions away from its intersection with the longitudinal bore 108. This configuration permits a small amount of swiveling of the transducer 96 within the horizontal plane to adjust the position thereof relative to the tube centerline.

Figure 49:
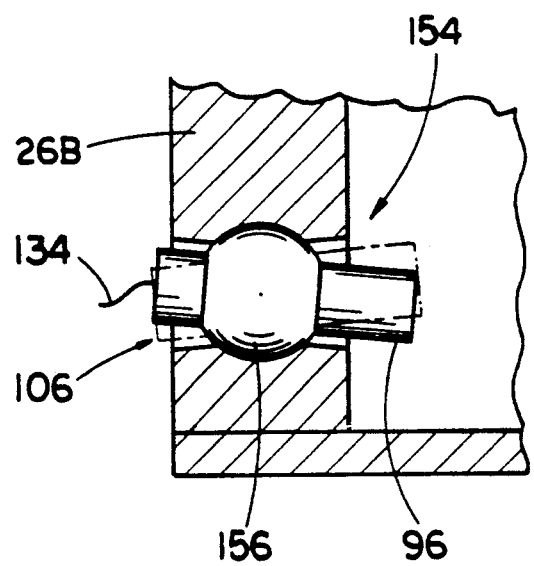
FIG. 49 is a view similar to that of FIG. 45 illustrating the range of horizontal swivel movement of the mounting bearing.
Figure 48:
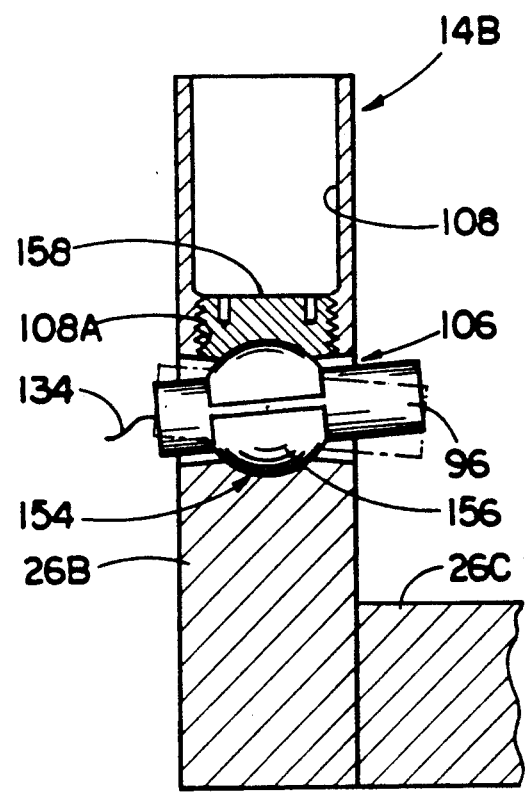
FIG. 48 is a view similar to that of FIG. 44 illustrating the range of vertical swivel movement of the mounting bearing.

Referring next to FIGS. 43 to 47, a second alternative embodiment of the tube parameter measuring means 16 is an adjustable longitudinal or transverse flaw transducer assembly 154 which includes the transducer 96 and mounting member in the form of a split spherical annular mounting bearing 156 capable of universal swivel movement. The longitudinal bore 108 in the receptacle side wall 26B is threaded at its lower end 108A. The mounting member also includes an externally-threaded plug 158 which forms the top half of a circular socket 160 for retaining the spherical mounting bearing 156 within the flared transverse bore 106. The transducer 96 is disposed through an opening 156A in the bearing 156. FIGS. 48 and 49 depict the respective ranges of swivel movement of the mounting bearing 156 in the vertical and horizontal planes.

Figure 51:
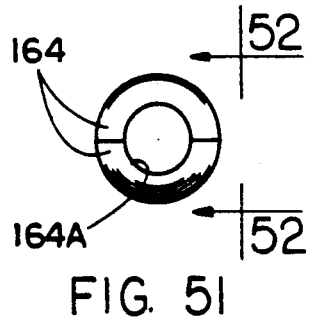
FIG. 51 is an end elevational view of a two-piece spherical mounting bearing of the inspection station adjustable transducer assembly of FIG. 50 removed from the assembly.
Figure 52:
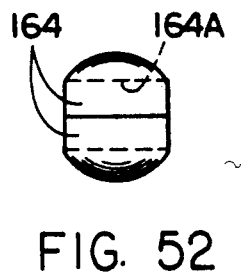
FIG. 52 is a side elevational view of the two-piece mounting bearing as seen along line 52—52 of FIG. 51.
Figure 50:
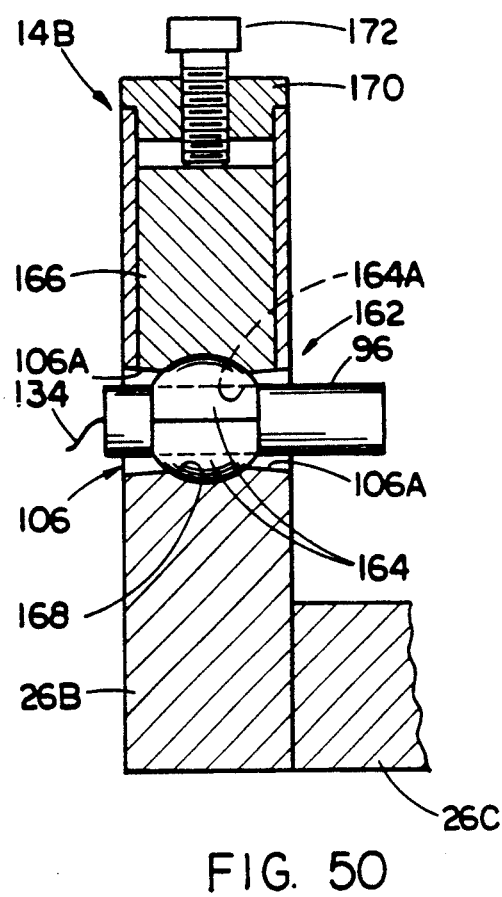
FIG. 50 is a fragmentary vertical sectional view of a tube flaw inspection station having still another embodiment of an adjustable longitudinal or transverse flaw transducer assembly in accordance with the present invention.

Referring now to FIGS. 50 to 52, a third alternative embodiment of the tube parameter measuring means 16 is an adjustable longitudinal or transverse flaw transducer assembly 162 which includes the transducer 96 and a mounting member having a two-piece spherical annular mounting bearing 164 capable of universal swivel movement. The mounting member also includes a cylindrical block 166 slidably mounted in the longitudinal bore 108 and having a lower end which forms the top half of a circular socket 168 for retaining the spherical mounting bearing 164 within the flared transverse bore 106. The transducer 96 is received through an opening 164A in the bearing 164. The mounting member also encompasses a cap 170 and a bolt 172. The cap 170 closes the upper mouth of the longitudinal bore 108 and mounts the threaded bolt 172. The bolt 172 is turned to force the block 166 against the mounting bearing 164 to hold it stationary.

Figure 54:
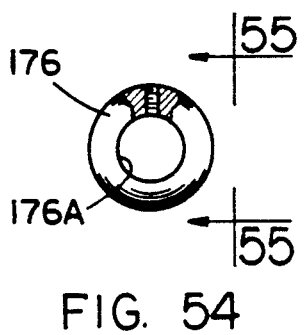
FIG. 54 is an end elevational view of an annular mounting bearing of the inspection station adjustable transducer assembly of FIG. 53 removed from the assembly.
Figure 55:
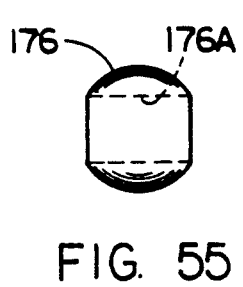
FIG. 55 is a side elevational view of the annular mounting bearing as seen along line 55—55 of FIG. 54.
Figure 53:
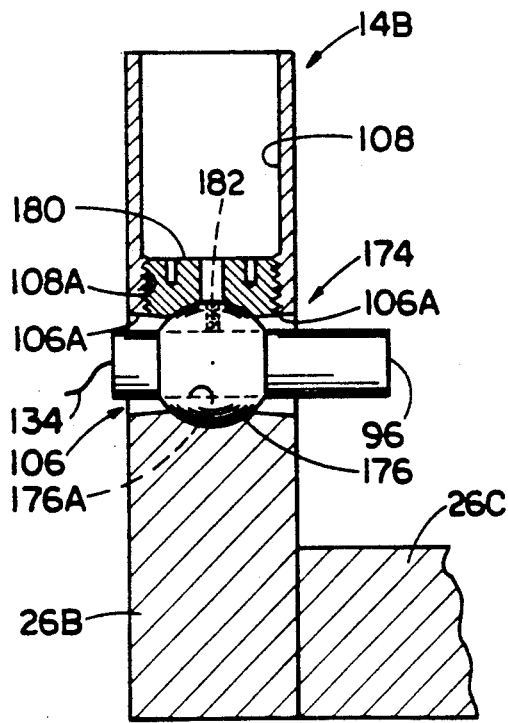
FIG. 53 is a fragmentary vertical sectional view of a tube flaw inspection station having yet another embodiment of an adjustable longitudinal or transverse flaw transducer assembly in accordance with the present invention.
Figure 61:
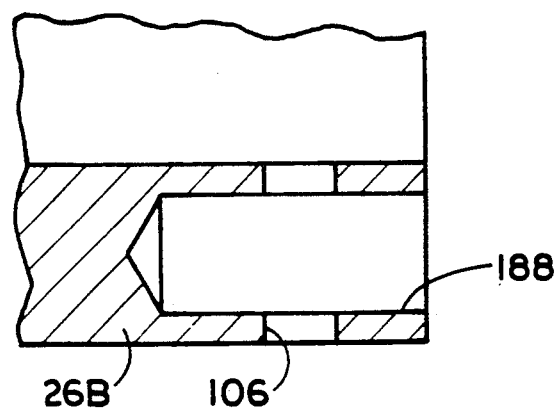
FIG. 61 is a fragmentary horizontal sectional view of the inspection station taken along line 61—61 of FIG. 60.
Figure 60:
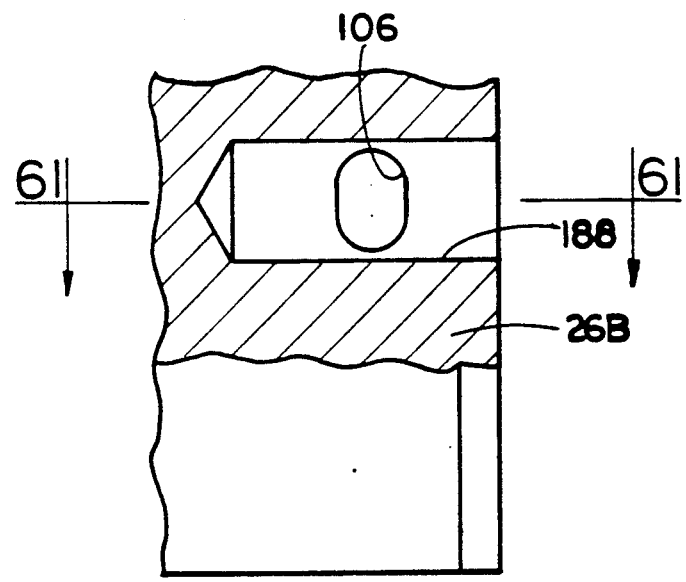
FIG. 60 is a fragmentary view of the inspection station of FIG. 56 with portions broken away and sectioned to illustrate a cylindrical bore of the station which receives the two-piece cylindrical mounting bearing.
Figure 59:
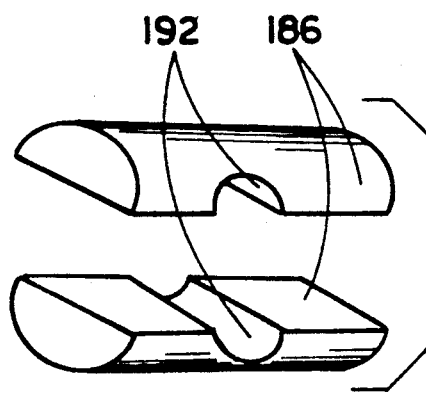
FIG. 59 is an exploded perspective view of the two-piece cylindrical mounting bearing of the inspection station adjustable transducer assembly of FIG. 57 removed from the assembly.

Referring next to FIGS. 53 to 55, a fourth alternative embodiment of the tube parameter measuring means 16 is an adjustable longitudinal or transverse flaw transducer assembly 174 which includes the transducer 96 and a mounting member in the form of an annular spherical mounting bearing 176 capable of universal swivel movement. The mounting member also includes a threaded plug 180 and set screw 182. The set screw 182 threads into the bearing 176 to retain the transducer 96. The plug 180 is substantially identical that the one in FIG. 44. The transducer 96 is received through an opening 176A in the bearing 176.

Referring finally to FIGS. 56, 57, 59 and 60, a fifth alternative embodiment of the tube parameter measuring means 16 is an adjustable longitudinal flaw transducer assembly 184 which includes the transducer 96 and a mounting member in the form of a two-piece cylindrical mounting bearing 186 capable of swivel movement in a horizontal plane within a cylindrical recess 188 formed in the side wall 26B extending orthogonal to the transverse bore 106. The mounting member also includes a set screw 190 which engages the mounting bearing 186 and holds it stationary. The cylindrical bearing 186 also has a central opening 192 for receiving and holding the transducer 96. FIG. 58 depicts the range of swivel movement of the two-piece cylindrical mounting bearing 186 in the horizontal plane.

Modified Arrangement of Inspection Stations

Figure 62:
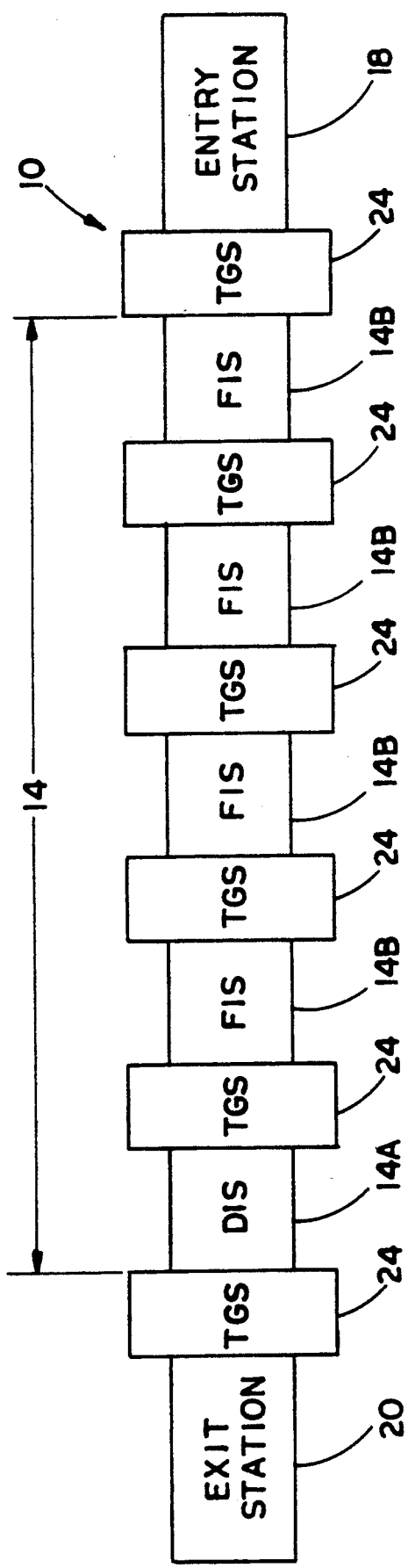
FIG. 62 is a diagrammatic representation of the tube inspection system in accordance with the invention of the above cross-referenced application having separate tube flaw inspection stations for inspecting different tube diameter sizes with each flaw inspection station having sets of transducer assemblies for both longitudinal and transverse flaw inspection.

Economy of space utilization is a desirable objective in inspection system design. FIG. 62 is a diagrammatic representation of the tube inspection system 10 of FIGS. 1 to 3 in accordance with the invention of the cross-referenced application. As described earlier, the inspection system 10 is a serial arrangement 14 of one tube dimension inspection station 14A, labelled DIS, with four tube flaw inspection stations 14B, labelled FIS. The inspection system 10 also includes entry and exit liquid level control stations 18, 20, labelled ENTRY STATION and EXIT STATION, and four tube guide stands 24, labelled TGS, which are interposed between the flaw inspection stations 14B and entry and exit control stations 18, 20. Thus, the inspection system 10 has separate tube flaw inspection stations 14B for inspecting different tube diameter sizes wherein each flaw inspection station 14B has transducer assemblies for both longitudinal and transverse flaw inspection.

Notwithstanding the significant advantages of the serial arrangement of multi-dimension tube flaw inspection stations 14B of the inspection system 12 which have been discussed earlier, it is still desirable to further minimize the distance between the tube drives 22 (FIGS. 1 to 3) located adjacent the ends of entry and exit stations 18, 20 so that shorter tubes can be driven through the system by at least one of the two drives. It is also desirable to make the system more compact to keep the distance between the tube guide supports 24 to a minimum in order to stabilize the tube and preclude any whipping or lateral tracking irregularities.

Figure 63:
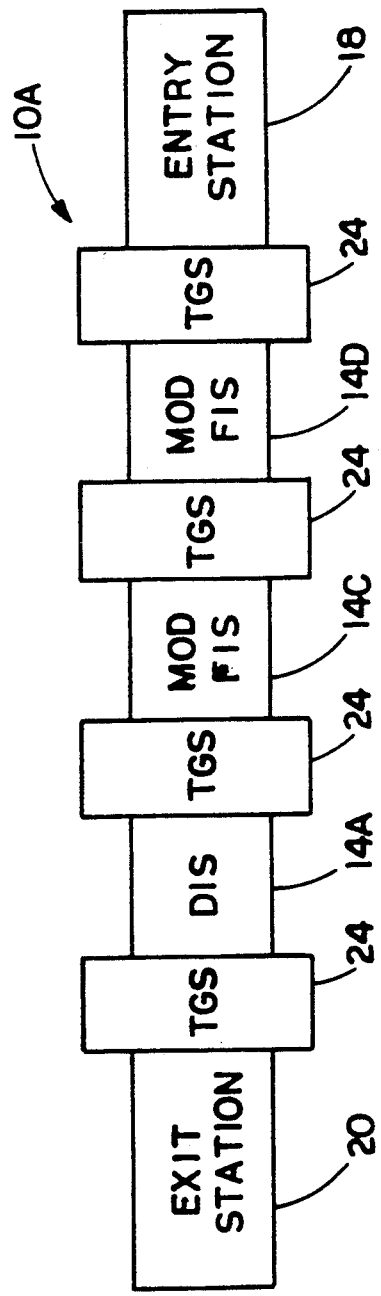
FIG. 63 is a diagrammatic representation of the tube inspection system in accordance with the present invention having one inspection station with multiple transducer assemblies oriented for longitudinal flaw inspection of tubes having the different diameter sizes and a separate inspection station with multiple transducer assemblies oriented for transverse flaw inspection of tubes having the different diameter sizes.

An alternative arrangement of transducer assemblies in which the assemblies for inspection of longitudinal and transverse flaws are differently grouped and arranged permits shortened of the overall length of the system. FIG. 63 is a diagrammatic representation of a modified tube inspection system 10A in accordance with another aspect of the present invention. The same single tube dimension inspection station 14A, entry and exit liquid level control stations 18, 20 and tube guide stands 14 are employed. However, the modified inspection system 10A has one modified tube flaw inspection station 14C, labelled MOD FIS, with multiple pairs of transducer assemblies oriented for transverse flaw inspection of tubes having the different diameter sizes and a separate modified tube flaw inspection station 14D, labelled MOD FIS also, with multiple pairs of transducer assemblies oriented for longitudinal flaw inspection of tubes having the different diameter sizes.

For measuring tubes of four different diameter sizes for transverse and longitudinal flaws, two sets of eight transducers each are used. The eight transverse flaw inspecting transducer assemblies 60 are arranged in one inspection station 14C and the eight longitudinal flaw inspecting transducer assemblies 58 are arranged in a separate inspection station 14D. FIG. 64 is a diagrammatic representation of one embodiment of the modified tube transverse flaw inspection station 14C with eight transverse flaw inspecting transducer assemblies 60. The pairs of transducer assemblies 60 that would be connected to the external electronic equipment in order to inspect a different tube diameter size are numbered the same. In arranging the transducer assemblies 60, it is necessary to avoid "crosstalk" and "shotgunning", wherein the sound waves from one transducer assembly is either picked up as an echo in another transducer assembly or as a misdirected or unknown lobe of direct sound. FIG. 65 is a slightly modified arrangement of the same transducer assemblies 60 from the arrangement of FIG. 64. FIG. 66 is a diagrammatic representation of one embodiment of the modified tube longitudinal flaw inspection station 14D with eight longitudinal flaw inspecting transducer assemblies 58. The pairs of transducer assemblies 58 that would be connected to the external electronic equipment in order to inspect a different tube diameter size are numbered the same.

The modified constructions of the transducer assemblies described earlier in reference to FIGS. 38 to 61 which permit swiveling of the transducers 94, 96 can be employed in the modified inspection stations 14C, 14D of FIGS. 64 to 66 as desired. The range of swiveling movement of the transducer assemblies 58, 60 are depicted in the figures also.

It is thought that the present invention and many of its attendant advantages will be understood from the foregoing description and it will be apparent that various changes may be made in the form, construction and arrangement of the parts of the invention described herein without departing from the spirit and scope of the invention or sacrificing all of its material advantages, the forms hereinbefore described being merely preferred or exemplary embodiments thereof.

We claim:

1. An inspection station, comprising the combination of:

(a) a receptacle having interconnected walls defining a cavity for holding energy coupling liquid and receiving an object to be inspected in the liquid, at least one wall having interior and exterior surfaces, a longitudinal bore defined between and spaced from said surfaces and extending within said one wall from an opening at the top of said one wall above said cavity, and a transverse bore extending through said one wall, said transverse bore intersecting with said longitudinal bore and open at both said interior and exterior surfaces of said one wall;

(b) a transducer having first and second opposite ends, said transducer being operable for sending waves of energy from said first end into said cavity toward the object and receiving echoes of energy at said first end from the object for measuring a parameter of the object, said transducer having means at said second end for transmitting input and output signals to and from said transducer; and (c) means removably mounted in said longitudinal and transverse bores of said one wall and removably mounting said transducer in said transverse bore of said one wall such that said first end of said transducer communicates with said cavity and said second end of said transducer communicates with the exterior of said receptacle, said mounting means including (i) an elongated cylinder having a transverse opening for insertion of said transducer and a central passage extending from said transverse opening to an upper end of said cylinder, said passage being internally threaded at a lower end; and (ii) means threadably received in said lower end of said passage in said cylinder for engaging and holding said transducer in said transverse opening of said cylinder.

2. The inspection station as recited in claim 1, wherein said mounting means further includes:

said cylinder being externally threaded at an upper end portion and defining an annulus between said longitudinal bore and exterior of said cylinder upper end portion;

an internally threaded end cap threadably receivable on said upper end portion of said cylinder and within said annulus such that rotation of said end cap will cause axial movement of said cylinder in said longitudinal bore to position the transducer within said transverse bore; and means for retaining said end cap at a stationary axial position with respect to said longitudinal bore while permitting rotation of said end cap.

3. The inspection station as recited in claim 2, wherein said mounting means further includes a spring located between a bottom end of said longitudinal bore and a bottom end of said mounting cylinder to assist in repositioning of said cylinder upon rotation of said end cap.

4. The inspection station as recited in claim 2, wherein said end cap has a peripheral groove and said retaining means is a plate having an edge which extends into said groove of said end cap for retaining said end cap in a stationary axial position relative to said longitudinal bore.

5. The inspection station as recited in claim 1, wherein said transverse bore has dual conical portions flaring in opposite direction away from its intersection with said longitudinal bore for permitting a swiveling movement of said transducer about the axis of said longitudinal bore within said transverse bore.

* * * * *